US010927095B2

(12) United States Patent
Luthra et al.

(10) Patent No.: US 10,927,095 B2
(45) Date of Patent: Feb. 23, 2021

(54) PROCESSES FOR THE PREPARATION OF NIRAPARIB AND INTERMEDIATES THEREOF

(71) Applicant: TEVA PHARMACEUTICALS INTERNATIONAL GMBH, Jona (CH)

(72) Inventors: Parven K. Luthra, New Delhi (IN); Sanjay L. Vasoya, Rajkot (IN); Bhatu T. Patil, Nandurbar (IN); Amit K. Taneja, Yamunanagar (IN); Naveen C. Srivastav, Sultanpur (IN); Rinku Singh, Noida (IN)

(73) Assignee: TEVA PHARMACEUTICALS INTERNATIONAL GMBH

( * ) Notice: Subject to any disclaimer, the term of this patent is extended or adjusted under 35 U.S.C. 154(b) by 0 days.

(21) Appl. No.: 16/638,821

(22) PCT Filed: Aug. 14, 2018

(86) PCT No.: PCT/US2018/046651
§ 371 (c)(1),
(2) Date: Feb. 13, 2020

(87) PCT Pub. No.: WO2019/036441
PCT Pub. Date: Feb. 21, 2019

(65) Prior Publication Data
US 2020/0190056 A1    Jun. 18, 2020

(30) Foreign Application Priority Data

Aug. 14, 2017 (IN) .............................. 201711028921
Oct. 27, 2017 (IN) .............................. 201711038212
Jun. 29, 2018 (IN) .............................. 201811024356

(51) Int. Cl.
*C07D 401/10* (2006.01)
*C07D 211/34* (2006.01)
*C07C 233/65* (2006.01)

(52) U.S. Cl.
CPC .......... *C07D 401/10* (2013.01); *C07C 233/65* (2013.01); *C07D 211/34* (2013.01)

(58) Field of Classification Search
CPC .......................... C07D 401/10; C07D 211/34
See application file for complete search history.

(56) References Cited

U.S. PATENT DOCUMENTS 5,482,941 A * 1/1996 Terrett .................... A61P 27/14
514/252.17

FOREIGN PATENT DOCUMENTS

WO    2008084261 A1    7/2008

OTHER PUBLICATIONS

Database Registry [Online] Chemical Abstracts Service; May 2, 2011, Database accession No. 1289162-62-4 (XP-002784888) 1 page.
Database Registry [Online] Chemical Abstracts Service; May 2, 2011, Database accession No. 1289113-01-4 (XP-002784889) 1 page.
Database Registry [Online] Chemical Abstracts Service; May 2, 2011, Database accession No. 1289036-29-8 (XP-002784890) 1 page.
International Preliminary Report on Patentability issued in corresponding Int'l Appl. PCT/US2018/046651 dated Feb. 27, 2020 (7 pages).
Communication pursuant to Rules 161(1) and 162 EPC issued in corresponding European Appl No. EP 18760237.0 dated Mar. 24, 2020 (3 pages).
International Search Report and Written Opinion issued in correspoding International Appl. No. PCT/US2018/046651 dated Oct. 29, 2018 (17 pages).

* cited by examiner

*Primary Examiner* — Niloofar Rahmani
(74) *Attorney, Agent, or Firm* — Carter, DeLuca & Farrell LLP

(57) ABSTRACT

The present invention relates to novel procedures and novel intermediates useful in the synthesis of Niraparib or any salt thereof.

17 Claims, 5 Drawing Sheets

PROCESSES FOR THE PREPARATION OF NIRAPARIB AND INTERMEDIATES THEREOF

CROSS REFERENCE TO RELATED APPLICATIONS

This application is a National Stage of, and claims priority to and the benefit of, International Patent Application No. PCT/US2018/046651 filed on Aug. 14, 2018, which, in turn, claims the benefit of, and priority to, Indian Application No. 201711028921 filed Aug. 14, 2017, Indian Application No. 201711038212 filed Oct. 27, 2017, and Indian Application No. 201811024356 filed Jun. 29, 2018, the entire disclosures of each of which are incorporated by reference herein.

FIELD OF THE INVENTION

The present disclosure provides new procedures and intermediates for the preparation of Niraparib.

BACKGROUND OF THE INVENTION

Niraparib has the chemical name 2-{4-[(3S)-Piperidin-3-yl]phenyl}-2H-indazole-7-carboxamide. Niraparib has the following chemical structure:

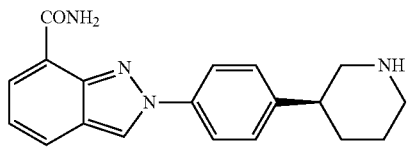 [SMILES: NC(=O)c1cccc2cn(-c3ccc([C@@H]4CCCNC4)cc3)nc12]

Niraparib tosylate is developed by TESARO Inc., for the maintenance treatment of adult patients with recurrent epithelial ovarian, fallopian tube, or primary peritoneal cancer, who are in a complete or partial response to platinum-based chemotherapy.

Niraparib is disclosed in WO 2007/113596 and WO 2008/084261 (U.S. counterpart U.S. Pat. No. 8,071,623 (referred to herein as U.S. '623 patent)). Niraparib tosylate monohydrate and Niraparib hydrochloride are also disclosed in U.S. '623. 4-Methylbenzenesulfonate (tosylate), sulfate, benzenesulfonate, fumarate, and succinate salts of Niraparib are disclosed in U.S. Pat. No. 8,436,185. Niraparib trifluoromethyl acetate is disclosed in U.S. Pat. No. 9,580,407 (referred to herein as U.S. '407 patent).

Processes for preparation of Niraparib and/or the intermediates are described in U.S. '623; U.S. '407 and US publication number 2016/0040201.

U.S. '623 discloses Niraparib and process for its preparation. U.S. '623 describes a process for the preparation of Niraparib, which involves chiral separation of 3-(4-aminophenyl)piperidine-1-carboxylate to obtain corresponding S-isomer, reaction of S-isomer with methyl 3-formyl-2-nitrobenzoate to obtain an imine, cyclisation in the presence of sodium azide to form indazole ring followed by amidation in presence of pyridine. The process is described in following Scheme-A:

Scheme: A

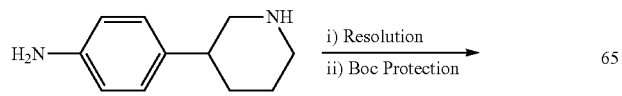

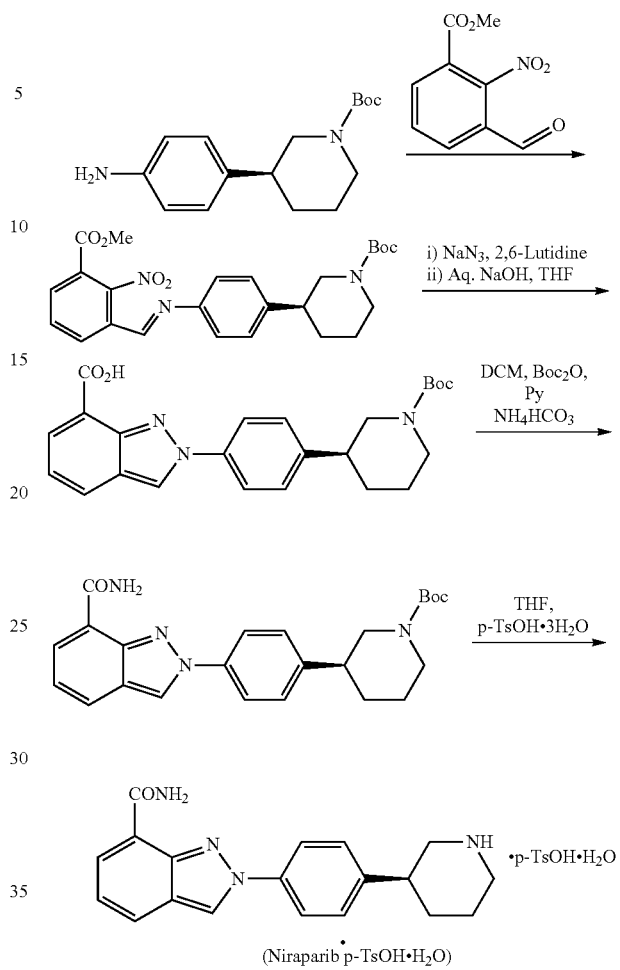

U.S. '407 discloses process for the preparation of Niraparib. The process is described in Scheme-B.

Scheme: B

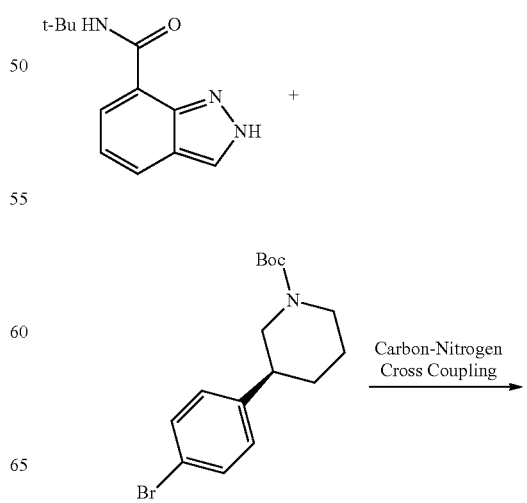

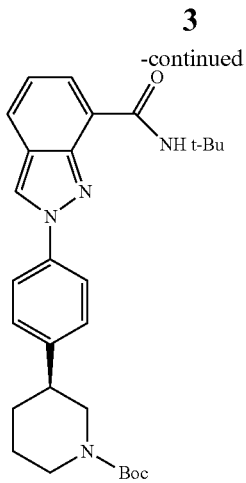

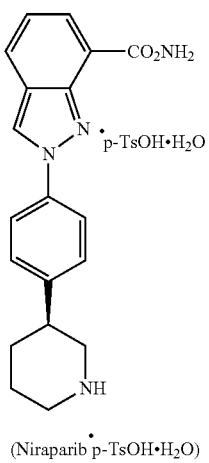

(Niraparib p-TsOH·H₂O)

The synthetic process disclosed in U.S. '407 patent involves preparation of Niraparib by carbon-nitrogen cross-coupling. It also involves column chromatography techniques for the purification and separation of intermediates.

US publication number 2016/0040201 discloses a process for the preparation of asymmetric intermediates of Niraparib by biocatalytic transamination in the presence of a transaminase polypeptide, a coenzyme, and an amino donor.

Organic Process Research Development (2011), 15(4), 831-840, discloses a method for the preparation of Niraparib by Suzuki coupling employing 3-pyridine boronic acid and p-nitroiodobenzene as raw materials.

Journal of Medicinal Chemistry (2009), 52(22), 7170-7185 also reports a process for the preparation of Niraparib involving use of chiral supercritical fluid liquid chromatography.

Therefore, there is a need in the art for improved processes for synthesizing Niraparib or any salt thereof with high yields, chemical purity and optical purity, which are suitable for industrial use.

SUMMARY OF THE INVENTION

The present disclosure provides novel intermediates, their preparation and their use in the preparation of Niraparib or any salt thereof.

The present disclosure provides processes for the preparation of Niraparib or any salt thereof.

The present disclosure provides a novel intermediate of formula (I) that can advantageously be used in the preparation of Niraparib or any salt thereof

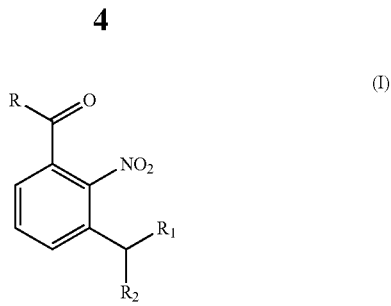

wherein; R is selected from the group consisting of: —O—R₃, and —NH—R₄;
R₁ and R₂ can independently be an alkoxy group or they can be connected to form a cyclic ring.
R₃ is hydrogen, $C_1$-$C_6$ alkyl, or a protecting group;
R₄ is hydrogen, or a protecting group;

More specifically, the present disclosure provides compounds of formula (2), (3), (4), (5) and (11) of the following structures:

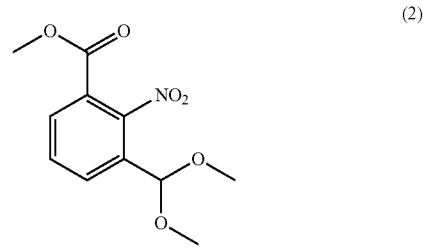

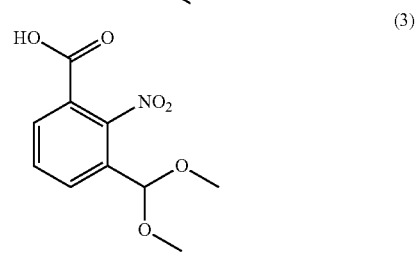

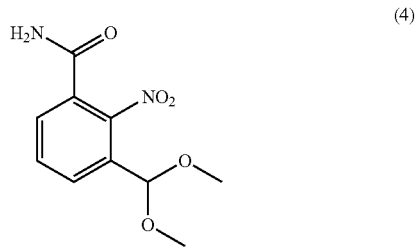

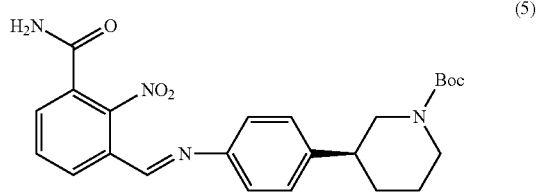

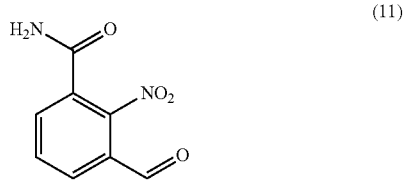

The present disclosure provides novel intermediates of formula (II) that can be advantageously used in the preparation of Niraparib

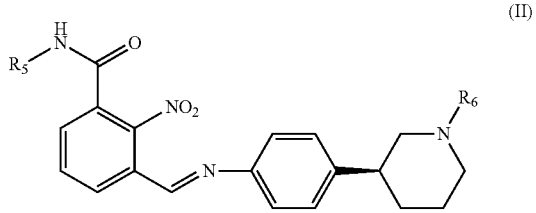

(II)

wherein; $R_5$ and $R_6$ can independently be hydrogen, $C_1$-$C_6$ alkyl, or a protecting group.

In another aspect the present disclosure provides isolated compounds of formula (I) and (II).

In another aspect, the isolated compounds of formula (I) and (II) are in solid state form.

The present disclosure also provides processes for preparing the compounds of formula (I) and (II), or the solid state forms thereof.

In an additional aspect, the disclosure relates to use of the compounds of formula (I) and (II) or the solid state forms thereof, in the preparation of Niraparib or any salt thereof.

In yet a further aspect, the disclosure provides processes for preparing Niraparib, comprising preparing compound of formula (I) or (II) or the solid state forms thereof according to the processes of the present disclosure and converting said compound of formula (I) or (II) or any one of the solid state forms thereof to Niraparib or any salt thereof.

In a further aspect, the disclosure relates to processes employing solid state forms of said intermediates for preparing Niraparib or any salt thereof.

In yet a further aspect, the disclosure provides Niraparib or any salt thereof prepared by the processes of the disclosure.

In a further aspect, Niraparib or any salt thereof prepared according to present disclosure is substantially pure.

In yet a further aspect, Niraparib or any salt thereof prepared according to present disclosure is substantially free of impurities The present disclosure also provides use of the Niraparib tosylate prepared according to present process for treating adult patients with recurrent epithelial ovarian, fallopian tube, or primary peritoneal cancer.

DETAILED DESCRIPTION OF THE INVENTION

Figure 1:
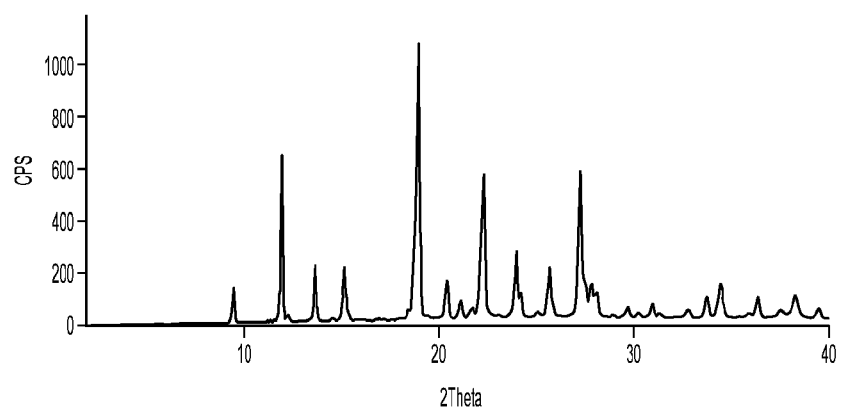
FIG. 1 shows an X-ray powder diffraction (XRPD) pattern of Form A of compound of formula (2), prepared according to process described in Example 1 (D).

The present disclosure provides new procedures and intermediates for the preparation of Niraparib or any salt thereof.

As discussed above, the processes described in the literature have significant disadvantages, such as the use of hazardous pyridine for the preparation of Niraparib. In addition, they involve column/chiral chromatography techniques for the purification and separation of intermediates and Niraparib. Other known processes involve the use of hazardous chemical and/or non-economical intermediates, as explained above. Also, the ester group is converted to amide group only in the last stages of the preparation of Niraparib, due to which there is yield loss in the final stage. In contrast, the processes of the present disclosure do not convert the ester group to amide group in the last stages, due to which there is an increase in the yield in the last stage of the preparation of Niraparib, making the process more cost effective.

In addition, Niraparib tosylate, in known processes, is prepared in tetrahydrofuran (THF) and water by an overnight reaction at higher temperature, which leads to the formation of impurities; while the present disclosure describes an improved process in which the reaction is performed at lower temperature for a shorter duration with an improved yield and purity.

Furthermore, according to processes described in the literature, during cyclisation step, hydrolysis product as an impurity is also formed along with other impurities, making work up and isolation difficult; while the present disclosure describes an improved process in which no hydrolysis product is formed. Niraparib or any salt thereof prepared according to present disclosure is substantially free of impurities.

Preparation of Niraparib involves carbon-nitrogen cross-coupling. The carbon-nitrogen cross-coupling of the known processes may lead to the formation of corresponding regioisomer as an impurity. The present disclosure describes an improved process for the preparation of Niraparib without carbon-nitrogen cross-coupling, which avoids the formation of regioisomer as an impurity. Further, few of the intermediates of the known processes, appear not to be stable and are liquid; which is not preferred for a large scale industrial process.

Furthermore, the processes for the preparation of Niraparib and intermediates thereof described in the literature involve several lengthy steps involving active reagents such as metals, which are difficult to operate and are not preferred for large scale production. The described Suzuki coupling involves use of expensive pyridine-3-boronic acid; and the product is separated by column chromatography. The further hydrogenation step employs expensive platinum reagents.

Thus, the reported processes may not be considered suitable for large scale production, as it reports use of chiral supercritical fluid liquid chromatography, and after repeated crystallization the yield is low.

As used herein, and unless indicated otherwise, the term "isolated" in reference to the intermediates of the present disclosure, their salts or solid state forms thereof corresponds to compounds that are physically separated from the reaction mixture in which they are formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

As used herein, and unless indicated otherwise, the term "one pot process" refers to a continuous process for preparing a desired product, in which penultimate product is converted to the desired product in the same vessel.

The processes or steps may be referred to herein as being carried out "overnight." This refers to time intervals, e.g., for the processes or steps, that span the time during the night, when the processes or steps may not be actively observed. The time intervals are from about 8 to about 20 hours, or about 10 to about 18 hours, or about 16 hours.

As used herein, and unless indicated otherwise, the term "reduced pressure" refers to a pressure of about 10 mbar to about 500 mbar, or about 50 mbar.

The amount of solvent employed in chemical processes, e.g., reactions or crystallizations, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding MTBE (1.5 v/v) to a 100 ml reaction mixture would indicate that 150 mL of MTBE was added.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of compound referred to herein as being characterized by graphical data "as depicted in" a Figure will thus be understood to include any crystal forms of the compound, characterized with the graphical data having such small variations, as are well known to the skilled person, in comparison with the Figure.

As used herein, unless stated otherwise, XRPD pattern peaks reported herein are optionally measured using CuK$_\alpha$ radiation, λ=1.5418 Å. Preferably, XRPD peaks reported herein are measured using CuK$_\alpha$ radiation, λ=1.54 Å, at a temperature of 25±3° C.

As used herein, and unless indicated otherwise, the term "substantially pure" relates to a compound, having a purity, measured as % area HPLC, of about 95% or more. In some embodiments, the term relates to compounds having a purity of about 95% or more. In other embodiments, the term relates to compounds having a purity of about 97% area by HPLC. In further embodiments, the term relates to compounds having a purity of about 99% area by HPLC. In yet other embodiments, the term relates to compounds having a purity of about 99.3% area by HPLC. In still further embodiments, the term relates to compounds having a purity of about 99.8% area by HPLC.

As used herein, and unless indicated otherwise, the term "substantially free of", referring to a compound of the present disclosure such as compounds I or II, or to any of the solid state forms of the present disclosure, means that the compounds or the solid state form contain about 20% (w/w) or less, about 10% (w/w) or less, about 5% (w/w) or less, about 4% (w/w) or less, about 3% (w/w) or less, about 2% (w/w) or less, about 1% (w/w) or less, about 0.5% (w/w) or less, or about 0.2% (w/w) or less or 0% of a specified impurity or any other forms of the subject compound as measured, for example, by XRFD, respectively. Thus, compounds or solid state form of compounds described herein as is substantially free of a specified impurity or any other solid state forms respectively, would be understood to contain greater than about 80% (w/w), greater than about 90% (w/w), greater than about 95% (w/w), greater than about 98% (w/w), greater than about 99% (w/w), or 100% of the subject compound or solid state form of compound. Accordingly, in some embodiments of the disclosure, the described compounds and solid state forms of intermediates may contain from about 1% to about 20% (w/w), from about 5% to about 20% (w/w), or from about 5% to about 10% (w/w) of one or more specified impurity or other solid state forms of the same intermediate, respectively.

As used herein, and unless indicated otherwise, the term "polar aprotic solvent" has a dielectric constant greater than 15 and is at least one selected from the group consisting of amide-based organic solvents, such as N,N-dimethylformamide (DMF), N,N-dimethylacetamide (DMA or DMAc), N-methylpyrrolidone (NMP), formamide, acetamide, propanamide, hexamethyl phosphoramide (HMPA), and hexamethyl phosphorus triamide (HMPT); nitro-based organic solvents, such as nitromethane, nitroethane, nitropropane, and nitrobenzene; pyridine-based organic solvents, such as pyridine and picoline; sulfone-based solvents, such as dimethylsulfone, diethylsulfone, diisopropylsulfone, 2-methylsulfolane, 3-methylsulfolane, 2,4-dimethylsulfolane, 3,4-dimethyl sulfolane, 3-sulfolene, and sulfolane; and sulfoxide-based solvents such as dimethylsulfoxide (DMSO).

As used herein, and unless indicated otherwise, the term "chlorinated solvent" refers to a $C_1$-$C_6$ chlorinated hydrocarbon. In some embodiments, the chlorinated solvents are selected from the group consisting of carbon tetrachloride, dichloromethane (DCM), dichloroethane, chlorobenzene, and chloroform.

As used herein, and unless indicated otherwise, the term "ether solvent" is an organic solvent containing an oxygen atom —O— bonded to two other carbon atoms. "Ether solvents" include, but are not limited to, diethyl ether, diisopropyl ether, methyl t-butyl ether (MTBE), glyme, diglyme, tetrahydrofuran (THF), 2-methyltetrahydrofuran (2-Me THF), 1,4-dioxane, dibutyl ether, dimethylfuran, 2-methoxyethanol, 2-ethoxyethanol, anisole, $C_2$-$C_6$ ethers, or the like.

As used herein, and unless indicated otherwise, the term "ester solvent" is an organic solvent containing a carboxyl group —(C=O)—O— bonded to two other carbon atoms. "Ester solvents" include, but are not limited to, ethyl acetate, n-propyl acetate, isopropyl acetate, n-butyl acetate, isobutyl acetate, t-butyl acetate, ethyl formate, methyl acetate, methyl propanoate, ethyl propanoate, methyl butanoate, ethyl butanoate, $C_3$-$C_6$ esters, or the like.

As used herein, and unless indicated otherwise, the term "ketone solvent" is an organic solvent containing a carbonyl group —(C=O)— bonded to two other carbon atoms. "Ketone solvents" include, but are not limited to, acetone, ethyl methyl ketone, diethyl ketone, methyl isobutyl ketone (MIBK), $C_3$-$C_6$ ketones, or the like.

As used herein, and unless indicated otherwise, the term "nitrile solvent" is an organic solvent containing a cyano —(C≡N) bonded to another carbon atom. "Nitrile solvents" include, but are not limited to, acetonitrile, propionitrile, $C_2$-$C_6$ nitriles, or the like.

As used herein, and unless indicated otherwise, the term "alcohol solvents" include, but are not limited to, methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol i.e. IPA), 2-methoxyethanol, 1-butanol, 2-butanol, iso-butyl alcohol, tert-butyl alcohol, 2-ethoxyethanol, diethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, glycerol, $C_1$-$C_6$ alcohols, or the like.

As used herein, and unless indicated otherwise, the term "hydrocarbon solvent" refers to a liquid, saturated hydrocarbon, which may be linear, branched, or cyclic. It is capable of dissolving a solute to form a uniformly dispersed solution. Examples of a hydrocarbon solvent include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, $C_5$-$C_8$ aliphatic hydrocarbons, and mixtures thereof.

As used herein, and unless indicated otherwise, the term "aromatic hydrocarbon solvent" refers to a liquid, unsaturated, cyclic, hydrocarbon containing one or more rings which has at least one 6-carbon ring containing three double bonds. Examples of an aromatic hydrocarbon solvent include, but are not limited to, benzene toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$ aromatic hydrocarbons, or mixtures thereof.

As used herein, and unless indicated otherwise, the term "organic base" is an organic compound, which acts as a base. Examples of such bases include, but are not limited to, trimethylamine (TEA), pyridine, diisopropylamine (DIPA), N,N-diisopropylethylamine (DIPEA or DIEA), N-methylmorpholine (NMM), 1,4-diazabicyclo[2.2.2]octane (DABCO), triethanolamine, tributylamine, lutidine, 4-dimethylamino pyridine (DMAP), diethanolamine, 4-methylmorpholine, dimethylethanolamine, tetra methylguanidine, morpholine, imidazole, 2-methylimidazole, 4-methylimidazole, tetra methylammonium hydroxide, tetraethylammonium hydroxide, N-methyl-1,5,9-triazabicyclo[4.4.0]decene, 1,8-diazabicyclo[5.4.0]undec-7-ene (DBU), dicyclo hexylamine, and picoline.

As used herein, and unless indicated otherwise, the term "protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996).

As used herein, and unless indicated otherwise; examples of "amine protecting group" refers to formyl, acetyl, trifluoroacetyl, benzyl, benzoyl, carbamate, benzyloxycarbonyl, p-methoxybenzyl carbonyl, tert-butoxycarbonyl, trimethylsilyl, 2-trimethylsilyl-ethanesulfonyl, trityl and substituted trityl groups, allyloxycarbonyl, 9-fluorenylmethyloxycarbonyl, nitro-veratryloxycarbonyl, p-methoxybenzyl and tosyl.

The present disclosure provides novel intermediate of formula (I) that can be advantageously used in the preparation of Niraparib or any salt thereof

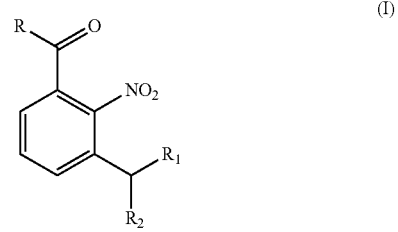

wherein; R is selected from the group consisting of: —O—$R_3$, and —NH—$R_4$;
$R_1$ and $R_2$ can independently be an alkoxy group or they can be connected to form a cyclic ring.
$R_3$ is hydrogen, $C_1$-$C_6$ alkyl, or a protecting group;
$R_4$ is hydrogen, or a protecting group;

The present disclosure provides novel intermediate of formula (II) that can be advantageously used in the preparation of Niraparib or any salt thereof

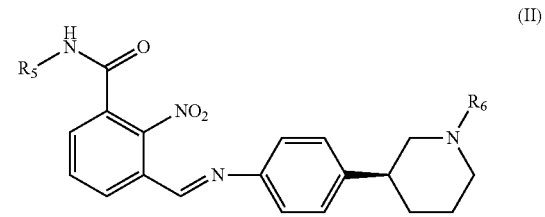

wherein; $R_5$ and $R_6$ can independently be hydrogen, $C_1$-$C_6$ alkyl, or a protecting group.

"Alkyl" refers to a monoradical of a branched or unbranched saturated hydrocarbon chain and can be substituted or unsubstituted. Lower alkyl groups may contain 1-6 carbon atoms or 1-4 carbon atoms. Examples of alkyl groups include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc.

"Alkoxy" refers to the O-(alkyl) group where the alkyl group is defined above.

As used herein, the "ring" formed with $R_1$ and $R_2$ refers to a 4- to 9-membered ring. Preferably, ring formed with $R_1$ and $R_2$ may be a 4- to 6-membered ring.

In one aspect, the present disclosure provides processes for preparing the compounds of formula (I) and (II).

In another aspect, the present disclosure provides isolated compounds of formula (I) and (II).

In another aspect, the isolated compounds of formula (I) and (II) are in solid state form.

The present disclosure also provides processes for preparing the solid state forms of compounds of formula (I) and (II).

In an additional aspect, the disclosure relates to use of the compounds of formula (I) and (II) in the preparation of Niraparib or any salt thereof.

In yet a further aspect, the disclosure provides process for preparing Niraparib, comprising preparing compound of formula (I) or (II) according to the processes of the present disclosure and converting compound of formula (I) or (II) to Niraparib or any salt thereof.

In another aspect, the disclosure relates to use of solid state forms of compounds of formula (I) and (II) in the preparation of Niraparib or any salt thereof.

In a further aspect, the disclosure relates to processes employing solid state forms of said intermediates for preparing Niraparib or any salt thereof.

In yet a further aspect, the disclosure provides process for preparing Niraparib, comprising preparing solid state forms of compound of formula (I) or (II) according to the processes of the present disclosure and converting solid state forms of compound of formula (I) or (II) to Niraparib or any salt thereof.

In some embodiments, the present disclosure provides compounds of formula (2), (3), (4), (5) and (11) of the following structures:

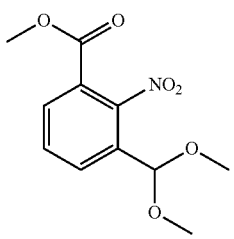
(2)

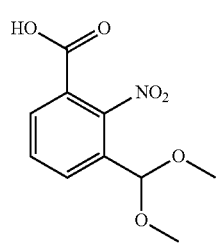
(3)

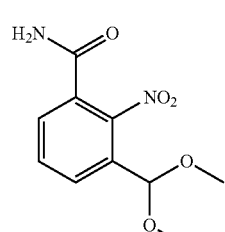
(4)

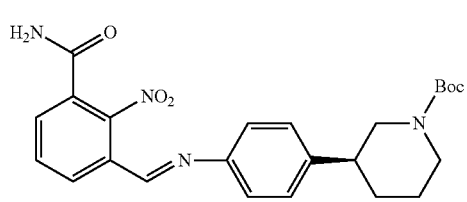
(5)

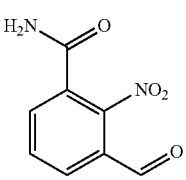
(11)

In certain embodiments, any one of compounds of formula (2), (3), (4), (5) and (11) is isolated in solid form. In other embodiments, any one of compounds of formula (2), (3), (4), (5) and (11) is crystalline.

The present disclosure comprises a crystalline form of compound of formula (2), designated as Form A. In certain embodiments, Form A of compound of formula (2) is isolated.

The crystalline Form A of compound of formula (2) can be characterized by data selected from one or more of the following: an XRPD pattern having peaks at 9.5, 11.9, 19.0, 22.3 and 27.3 degrees 2-theta±0.2 degrees 2-theta; an XRPD pattern as depicted in FIG. 1; or combinations of these data. Crystalline Form A of compound of formula (2) may be further characterized by the XRPD pattern having peaks at 9.5, 11.9, 19.0, 22.3 and 27.3 degrees 2-theta±0.2 degrees 2-theta; and also having one, two, three, four or five additional peaks selected from the group consisting of 13.7, 15.2, 20.4, 24.0 and 25.7 degrees two theta±0.2 degrees two theta.

Crystalline Form A of compound of formula (2) may be characterized by each of the above characteristics alone/or by all possible combinations, e.g. by an XRPD pattern having peaks at 9.5, 11.9, 19.0, 22.3 and 27.3 degrees 2-theta±0.2 degrees 2-theta and an XRPD pattern as depicted in FIG. 1.

The present disclosure comprises a crystalline form of compound of formula (3), designated as Form A. In certain embodiments, Form A of compound of formula (3) is isolated.

Figure 2:
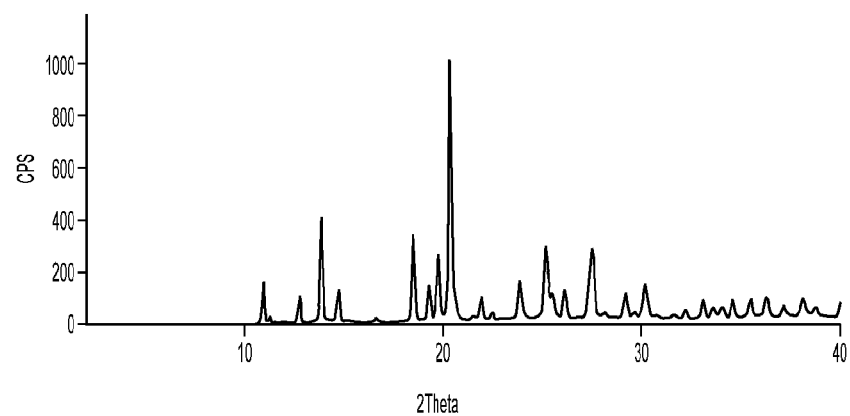
FIG. 2 shows an XRPD pattern of Form A of compound of formula (3), prepared according to process described in Example 1 (E).

The crystalline Form A of compound of formula (3) can be characterized by data selected from one or more of the following: an XRPD pattern having peaks at 10.9, 13.8, 18.5, 20.4 and 27.5 degrees 2-theta±0.2 degrees 2-theta; an XRPD pattern as depicted in FIG. 2; or combinations of these data. Crystalline Form A of compound of formula (3) may be further characterized by the XRPD pattern having peaks at 10.9, 13.8, 18.5, 20.4 and 27.5 degrees 2-theta±0.2 degrees 2-theta; and also having one, two, three, four or five additional peaks selected from the group consisting of 12.7, 19.8, 21.9, 23.9 and 25.2 degrees two theta±0.2 degrees two theta.

Crystalline Form A of compound of formula (3) may be characterized by each of the above characteristics alone/or by all possible combinations, e.g. by an XRPD pattern having peaks at 10.9, 13.8, 18.5, 20.4 and 27.5 degrees 2-theta±0.2 degrees 2-theta and an XRPD pattern as depicted in FIG. 2.

The present disclosure comprises a crystalline form of compound of formula (4), designated as Form A. In certain embodiments, Form A of compound of formula (4) is isolated.

Figure 3:
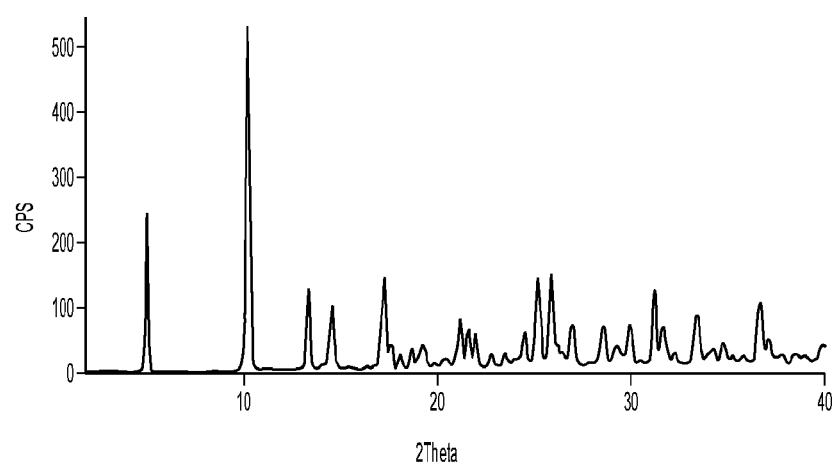
FIG. 3 shows an XRPD pattern of Form A of compound of formula (4), prepared according to process described in Example 1 (G).

The crystalline Form A of compound of formula (4) can be characterized by data selected from one or more of the following: an XRPD pattern having peaks at 5.1, 10.3, 13.4, 14.6 and 17.3 degrees 2-theta±0.2 degrees 2-theta; an XRPD pattern as depicted in FIG. 3; or combinations of these data. Crystalline Form A of compound of formula (4) may be further characterized by the XRPD pattern having peaks at 5.1, 10.3, 13.4, 14.6 and 17.3 degrees 2-theta±0.2 degrees 2-theta; and also having one, two, three, four or five additional peaks selected from the group consisting of 21.3, 25.2, 25.9, 27.0 and 31.2 degrees two theta±0.2 degrees two theta.

Crystalline Form A of compound of formula (4) may be characterized by each of the above characteristics alone/or by all possible combinations, e.g. by an XRPD pattern having peaks at 5.1, 10.3, 13.4, 14.6 and 17.3 degrees 2-theta±0.2 degrees 2-theta and an XRPD pattern as depicted in FIG. 3.

The present disclosure comprises a crystalline form of compound of formula (5), designated as Form A. In certain embodiments, Form A of compound of formula (5) is isolated.

Figure 4:
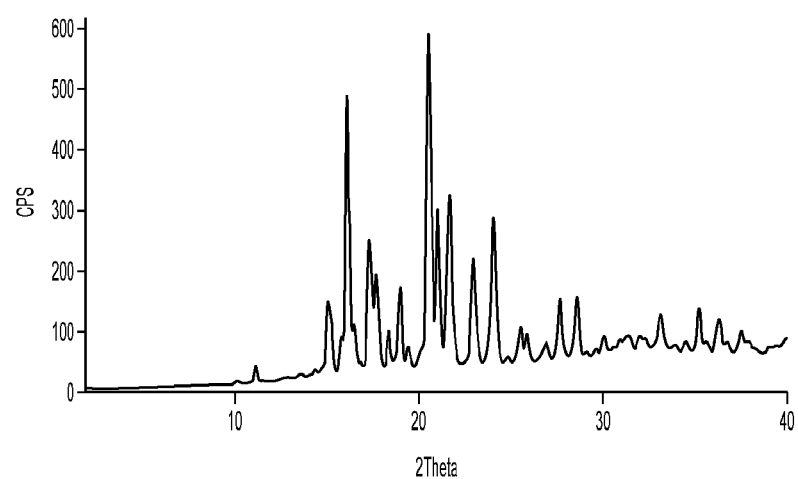
FIG. 4 shows an XRPD pattern of Form A of compound of formula (5), prepared according to process described in Example 3 (A).

The crystalline Form A of compound of formula (5) can be characterized by data selected from one or more of the following: an XRPD pattern having peaks at 16.2, 20.7, 21.7, 23.0 and 24.1 degrees 2-theta±0.2 degrees 2-theta; an XRPD pattern as depicted in FIG. 4; or combinations of these data. Crystalline Form A of compound of formula (5) may be further characterized by the XRPD pattern having peaks at 16.2, 20.7, 21.7, 23.0 and 24.1 degrees 2-theta±0.2 degrees 2-theta; and also having one, two, three, four or five additional peaks selected from the group consisting of 11.1, 15.1, 19.1, 27.7 and 28.6 degrees two theta±0.2 degrees two theta.

Crystalline Form A of compound of formula (5) may be characterized by each of the above characteristics alone/or by all possible combinations, e.g. by an XRPD pattern having peaks at 16.2, 20.7, 21.7, 23.0 and 24.1 degrees 2-theta±0.2 degrees 2-theta and an XRPD pattern as depicted in FIG. 4.

The present disclosure comprises a crystalline form of compound of formula (11), designated as Form A. In certain embodiments, Form A of compound of formula (11) is isolated.

Figure 5:
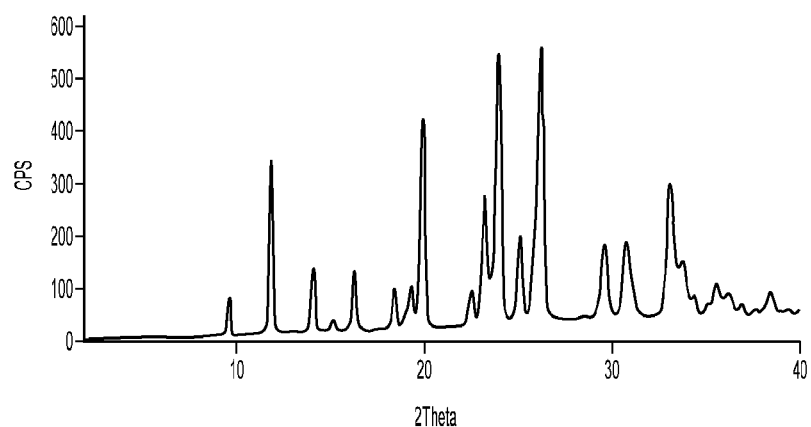
FIG. 5 shows an XRPD pattern of Form A of compound of formula (11), prepared according to process described in Example 1 (C).

The crystalline Form A of compound of formula (11) can be characterized by data selected from one or more of the following: an XRPD pattern having peaks at 11.9, 20.1, 24.1, 26.3 and 29.7 degrees 2-theta±0.2 degrees 2-theta; an XRPD pattern as depicted in FIG. 5; or combinations of these data. Crystalline Form A of compound of formula (11) may be further characterized by the XRPD pattern having peaks at 11.9, 20.1, 24.1, 26.3 and 29.7 degrees 2-theta±0.2 degrees 2-theta; and also having one, two, three, four or five additional peaks selected from the group consisting of 9.6, 14.1, 16.3, 25.2 and 30.8 degrees two theta±0.2 degrees two theta.

Crystalline Form A of compound of formula (11) may be characterized by each of the above characteristics alone/or by all possible combinations, e.g. by an XRPD pattern having peaks at 11.9, 20.1, 24.1, 26.3 and 29.7 degrees 2-theta±0.2 degrees 2-theta and an XRPD pattern as depicted in FIG. 5.

The above described solid state forms of intermediates of Niraparib can be used to prepare other corresponding solid state forms of intermediate of Niraparib.

The present disclosure further encompasses processes for preparing other solid state forms of intermediates of Niraparib. The processes comprise preparing a solid state form of the present disclosure, and converting it to another solid state form of intermediates of Niraparib.

In another embodiment, any one of compounds of formula (2), (3), (4), (5) and (11) is substantially pure.

In some embodiments, the disclosure provides the use of any one of compounds of formula (2), (3), (4), (5) and (11) as described above for the preparation of Niraparib or any salt thereof.

In a preferred embodiment, the disclosure provides solid state forms of compounds of formula (2), (3), (4), (5) and (11) for use in the preparation of Niraparib or any salt thereof.

In another embodiment, Niraparib or any salt thereof prepared according to present disclosure is substantially pure.

In another embodiment, Niraparib or any salt thereof prepared according to present disclosure is substantially free of impurities.

In a preferred embodiment, Niraparib or any salt thereof prepared according to present disclosure is substantially free of impurities of following formula (6), (7), (17) and (Va):

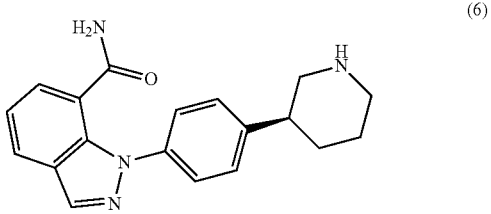

(6)

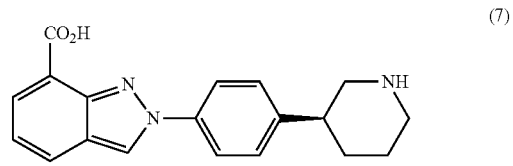

(7)

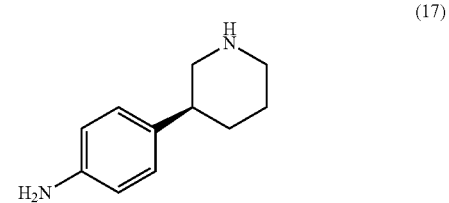

(17)

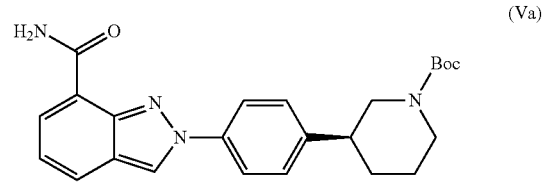

(Va)

In another embodiment, the present disclosure provides processes for the preparation of the following intermediates of Niraparib as depicted in Scheme 1:

Scheme: 1

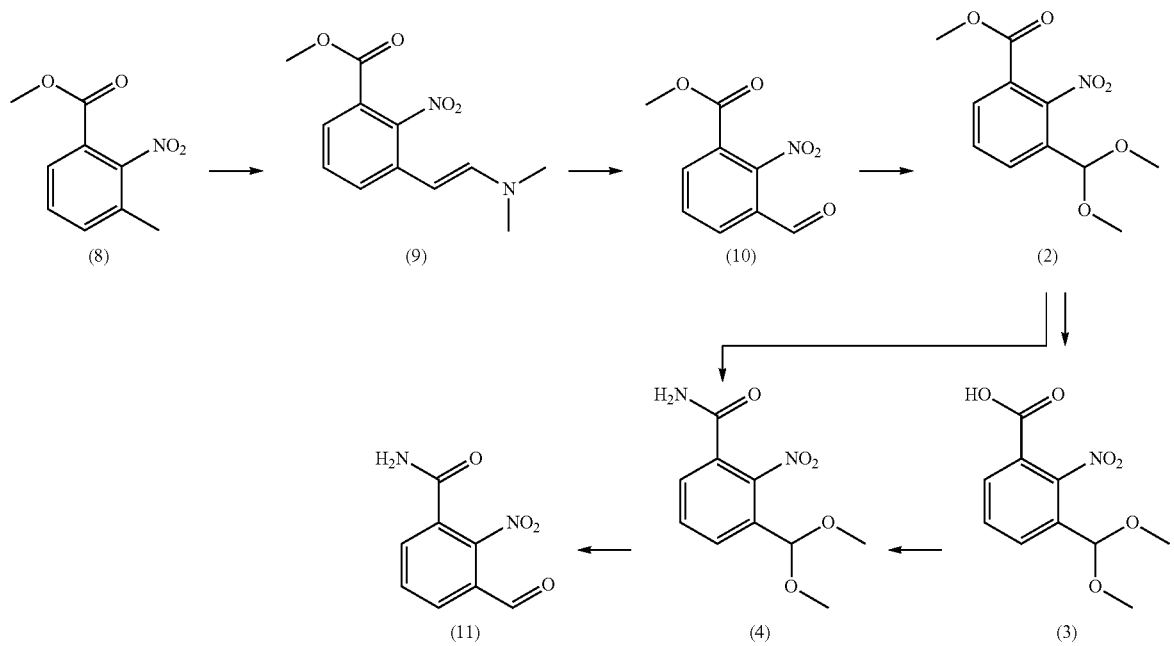

The step for the preparation of compound of formula (9) by reacting methyl 3-methyl-2-nitrobenzoate with dimethylformamide dimethylacetal (DMF-DMA) is carried out in a suitable solvent at suitable temperature.

Suitable solvents may include, but are not limited to, polar aprotic solvents, such as DMF, DMSO, DMAc, or the like, or any mixtures thereof. Preferably, the solvent may be DMF.

The process may be carried out at a temperature from about 90° C. to about 150° C., preferably at about 100° C. to about 130° C., and most preferably at about 125° C. to about 130° C.

Compound of formula (10) is prepared from compound of formula (9) in the presence of an oxidizing agent in a suitable solvent, optionally in the presence of pyrrolidine.

The oxidizing agent may include, but are not limited to sodium periodate or $KMnO_4$.

Suitable solvents may include, but are not limited to polar aprotic solvent, water, or the like. Preferably, the solvent may be selected from the group comprising of DMF, DMSO, DMA, water and any mixtures thereof.

The process may be carried out at a temperature from about 30° C. to about 60° C.; preferably at about 40° C. to about 45° C.

The above process for the preparation of compound of formula (10) can be done either as a one pot reaction; meaning, compound of formula (10) can be prepared from methyl 3-methyl-2-nitrobenzoate without isolating compound of formula (9). Alternatively, the compound of formula (9) can be isolated prior to its conversion to compound of formula (10).

Compound of formula (2) is prepared by the reaction of compound of formula (10) with a protecting agent in the presence of an acid in a suitable solvent at suitable temperature.

The said acid may include, but are not limited to, methanesulfonic acid (MSA), p-toluenesulfonic acid (PTSA), sulphuric acid, or the like, or any mixtures thereof, preferably methanesulfonic acid.

The said protecting agent may include, but are not limited to, for example $C_1$ to $C_4$ mono-hydroxy/di-hydroxy alcohols, such as methanol, ethanol, ethylene glycol, neo pentyl glycol. Preferably the alcohol may be methanol.

Suitable solvents that may be used include, but are not limited to: alcohol solvents, e.g., methanol, ethanol, 2-propanol, 1-propanol, 1-butanol, 2-butanol, or the like; hydrocarbon solvents/aromatic hydrocarbon solvent, e.g., toluene, xylene, cyclohexane, or the like; chlorinated solvents, e.g., dichloromethane (DCM), dichloroethane or the like; ether solvents, e.g., MTBE, THF, 2-Me THF or the like; or any mixtures thereof. Preferably, the solvent may be methanol or ethanol.

The said $C_1$ to $C_4$ mono-hydroxy/di-hydroxy alcohols may be used as protecting agent as well as suitable solvent. Preferably the alcohol may be methanol.

The process may be carried out at a temperature from about RT to about reflux temperature, preferably at about 50° C. to about 60° C.

Compound of formula (2) can be isolated; or used in the next step without isolation.

Compound of formula (4) is prepared by amidation of compound of formula (2) in the presence of ammonia in a suitable solvent at suitable pressure and suitable temperature.

The suitable solvent may include, but are not limited to, for example $C_1$ to $C_4$ mono-hydroxy/di-hydroxy alcohols, such as methanol, ethanol, ethylene glycol, and neo pentyl glycol. Preferably the alcohol may be methanol.

The process may be carried out at a temperature from about 20° C. to about 70° C. Preferably the process may be carried out at temperature of about 65° C. to about 70° C.

The process may be carried out at about 2 $Kg/cm^2$ to about 10 $Kg/cm^2$ pressure of ammonia gas. Preferably the process may be carried out at about 2 $Kg/cm^2$ of pressure of ammonia gas.

Compound of formula (4) may also be prepared by reaction of compound of formula (2) in the presence of a suitable amidation agent, acid activating agent and a base in a suitable solvent at a suitable temperature.

Suitable amidation agents may include, but are not limited to, ammonium bicarbonate, ammonia in solvent, ammonium carbonate, or any other source of ammonia.

Suitable acid activating agents may include, but are not limited to, 1,1'-carbonyldiimidazole (CDI), ethyl chloroformate (ECF), di-tert-butyl dicarbonate (boc anhydride), pivaloyl chloride, SOCl$_2$, or the like, or any mixtures thereof.

The suitable base may include, but are not limited to, organic base e.g. trimethylamine (TEA), pyridine, diisopropylamine (DIPA), N,N-diisopropylethylamine (DIPEA or DIEA), N-methylmorpholine (NMM), or the like, or any mixtures thereof.

Suitable solvents that may be used include, but are not limited to: alcohol solvents, hydrocarbon solvents/aromatic hydrocarbon solvents, chlorinated solvents, ether solvents, or the like. Preferably, the solvent may be selected from the group comprising of toluene, xylene, DCM, MTBE, and any mixtures thereof.

The process may be carried out at a temperature from about 0° C. to about 50° C., preferably at about 20° C. to about 30° C.

The compound of formula (3) is prepared by hydrolysis of compound of formula (2) in suitable solvent at a suitable temperature. Preferably, the hydrolysis may be carried out in presence of a suitable base.

A suitable base may include, but is not limited to, organic base or inorganic base or any mixtures thereof. Preferably, the base may be potassium hydroxide, sodium hydroxide, potassium tert-butoxide, triethylamine, or the like, or any mixtures thereof.

The amount of base employed for hydrolysis may range from about 1 equivalent to about 5 equivalents with respect to compound of formula (2); preferably 4 equivalents of base may be used.

Suitable solvents that may be used include, but are not limited to: water, alcohol solvents, polar aprotic solvents, ether solvents, ester solvents, hydrocarbon solvents/aromatic hydrocarbon solvents, chlorinated solvents, or the like. Preferably, the solvent may be selected from the group comprising of water, methanol, ethanol, isopropyl alcohol, butanol, THF, 2-Me-THF, DMF, DMA, ethyl acetate, isopropyl acetate, and any mixtures thereof.

The process may be carried out at a temperature from about 0° C. to about 100° C., preferably at about 50° C. to about 55° C.

The compound of formula (11) is prepared by deprotection of compound of formula (4) in suitable solvent at a suitable temperature. Preferably, the deprotection may be carried out in presence of a suitable acid.

The suitable acid may include, but are not limited to, organic acid or inorganic acid or any mixtures thereof. Preferably, the acid may be hydrochloric acid, sulphuric acid, p-toluenesulfonic acid (PTSA), trifluoro acetic acid (TFA), phosphoric acid, acetic acid or the like, or any mixtures thereof.

Suitable solvents that may be used include, but are not limited to: water, alcohol solvents, ether solvents, ester solvents, hydrocarbon solvents/aromatic hydrocarbon solvents, or the like. Preferably, the solvent may be selected from the group comprising of water, methanol, ethanol, isopropyl alcohol, butanol, tetrahydrofuran (THF), 2-Me-THF, and any mixtures thereof.

The process may be carried out at a temperature from about 0° C. to about 100° C., preferably at about 60° C. to about 65° C.

The above process for the preparation of compound of formula (11) can be done either as a one pot reaction; meaning, compound of formula (11) can be prepared from compound of formula (10) without isolating compounds of formula (2), (3) or (4). Alternatively, the compounds of formula (2), (3) or (4) can be isolated prior to its conversion to compound of formula (11).

In another embodiment, the present disclosure provides following processes for the preparation of Niraparib tosylate monohydrate and intermediates thereof as depicted in Scheme 2:

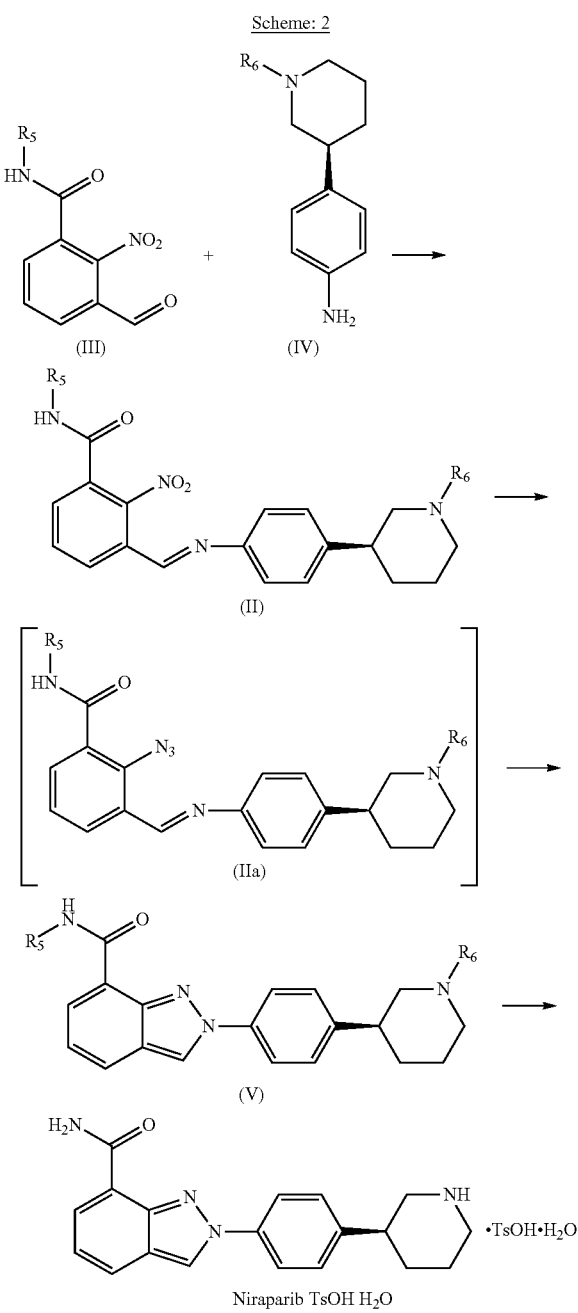

wherein; R$_5$ and R$_6$ can independently be hydrogen, C$_1$-C$_5$ alkyl, and a protecting group.

The step for the preparation of compound of formula (II) by reacting compound of formula (III) with compound of formula (IV) is carried out in a suitable solvent at suitable temperature.

Suitable solvents that may be used include, but are not limited to: polar aprotic solvents, alcohol solvents, ether solvents, nitrile solvents, hydrocarbon solvents, aromatic hydrocarbon solvents, or the like, and particularly alcohol solvents, ether solvents, nitrile solvents, hydrocarbon solvents, aromatic hydrocarbon solvents, or the like. The solvents can be selected from the group consisting of: dimethylformamide, N,N-dimethyl acetamide, dimethylsulfoxide, methanol, ethanol, isopropyl alcohol, butanol, acetonitrile, toluene, methyl t-butyl ether, and any mixtures thereof. Preferably, the solvent may be selected from the group comprising of methanol, ethanol, isopropyl alcohol, butanol, acetonitrile, toluene, MTBE, or the like, and any mixtures thereof.

The process may be carried out at a temperature from about 0° C. to about 140° C. Preferably, the process may be carried out at a temperature from about 0° C. to about 100° C., preferably at about 40° C. to reflux temperature.

The step for the cyclisation of compound of formula (II) for the preparation of compound of formula (V) is carried out by employing tetrabutyl ammonium azide, sodium azide or tri-n-butyl phosphine or the like in a suitable solvent at a suitable temperature, optionally in the presence of a suitable base. Preferably, the step for the cyclisation of compound of formula (II) for the preparation of compound of formula (V) is carried out by employing sodium azide or tri-n-butyl phosphine or the like in a suitable solvent at a suitable temperature, optionally in the presence of a suitable base.

Suitable solvents that may be used include, but are not limited to: alcoholic solvents, aromatic hydrocarbon solvent, polar aprotic solvents, or the like. Preferably, the solvent may be selected from the group comprising of DMF, DMA, NMP, DMSO, IPA, methanol, ethanol, 2-butanol, toluene or the like, and any mixtures thereof.

The process may be carried out at a temperature from about 100° C. to about 150° C., preferably at about 100° C. to about 120° C.

Suitable base that may be used includes, but is not limited to, organic base or inorganic base or any mixtures thereof. Preferably, the base may be 2,6-luitidine, triethylamine, N,N-diisopropylethylamine (DIPEA or DIEA), sodium hydroxide, potassium hydroxide, potassium carbonate, or the like, or any mixtures thereof. Most preferably, the base may be DIPEA or 2,6-luitidine.

The cyclisation of compound of formula (II) for the preparation of compound of formula (V) described above may be carried out without a base.

In a preferred embodiment, the step for the cyclisation of compound of formula (II) for the preparation of compound of formula (V) according to present disclosure is carried out in the presence of a suitable catalyst.

Suitable catalysts that may be used include, but are not limited to metal catalyst. Preferably, the metal catalyst may be copper catalysts, or the like. Suitable copper catalysts may be selected from the group consisting of copper acetate CuI, CuBr, CuCl or the like, and any mixtures thereof. Most preferably, the copper catalyst may be selected from the group comprising of CuI, CuBr, CuCl or the like, and any mixtures thereof.

The preparation of the compound of formula (V) may be carried out as a one pot reaction without isolating the compound of formula (II). Alternatively, the compound of formula (II) may be isolated prior to its conversion to compound of formula (V)

In another embodiment, compound of formula (V) prepared by the cyclisation of compound of formula (II) in the presence of a suitable catalyst according to present disclosure is substantially free of impurity of following formula (5a):

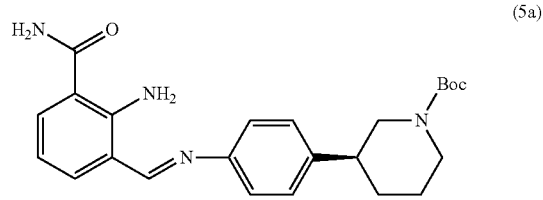 [SMILES: CC(C)(C)OC(=O)N1CCC[C@@H](c2ccc(/N=C/c3cccc(C(N)=O)c3N)cc2)C1]

(5a)

In another embodiment, the compound of formula (V) prepared by the cyclisation of compound of formula (II) in the presence of a suitable catalyst according to present disclosure is substantially pure with increased yield.

The above process for the preparation of compound of formula (V) can be done either as a one pot reaction; meaning, compound of formula (V) can be prepared from reaction of compound of formula (III) and (IV) without isolating compounds of formula (II). Alternatively, the compounds of formula (II) can be isolated prior to its conversion to compound of formula (V).

The process of the present disclosure may further comprise a step wherein the protected nitrogen of the compound of formula (V) is deprotected by a suitable deprotecting agent in a suitable solvent.

Suitable deprotecting agent that may be used include, but are not limited to, p-toluenesulfonic acid (PTSA), methanesulfonic acid (MSA), hydrochloric acid, sulphuric acid, acetic acid, phosphoric acid, trifluoro acetic acid (TFA); preferably p-toluenesulfonic acid (PTSA), methanesulfonic acid (MSA).

Suitable solvents that may be used include, but are not limited to: water, ether solvents, ketone solvent, ester solvents, hydrocarbon solvents/aromatic hydrocarbon solvents, chlorinated solvents, alcoholic solvents, nitrile solvent or the like. Preferably, the solvent may be selected from the group comprising of water, methanol, acetonitrile, acetone, THF, 2-Me-THF, toluene, cyclohexane, xylene, MIBK, MTBE, ethyl acetate, dichloromethane, and any mixtures thereof.

In another embodiment, the present disclosure provides following processes for the preparation of compound of formula (21) (Compound IV, R is Boc) as depicted below in Scheme 3:

Scheme: 3

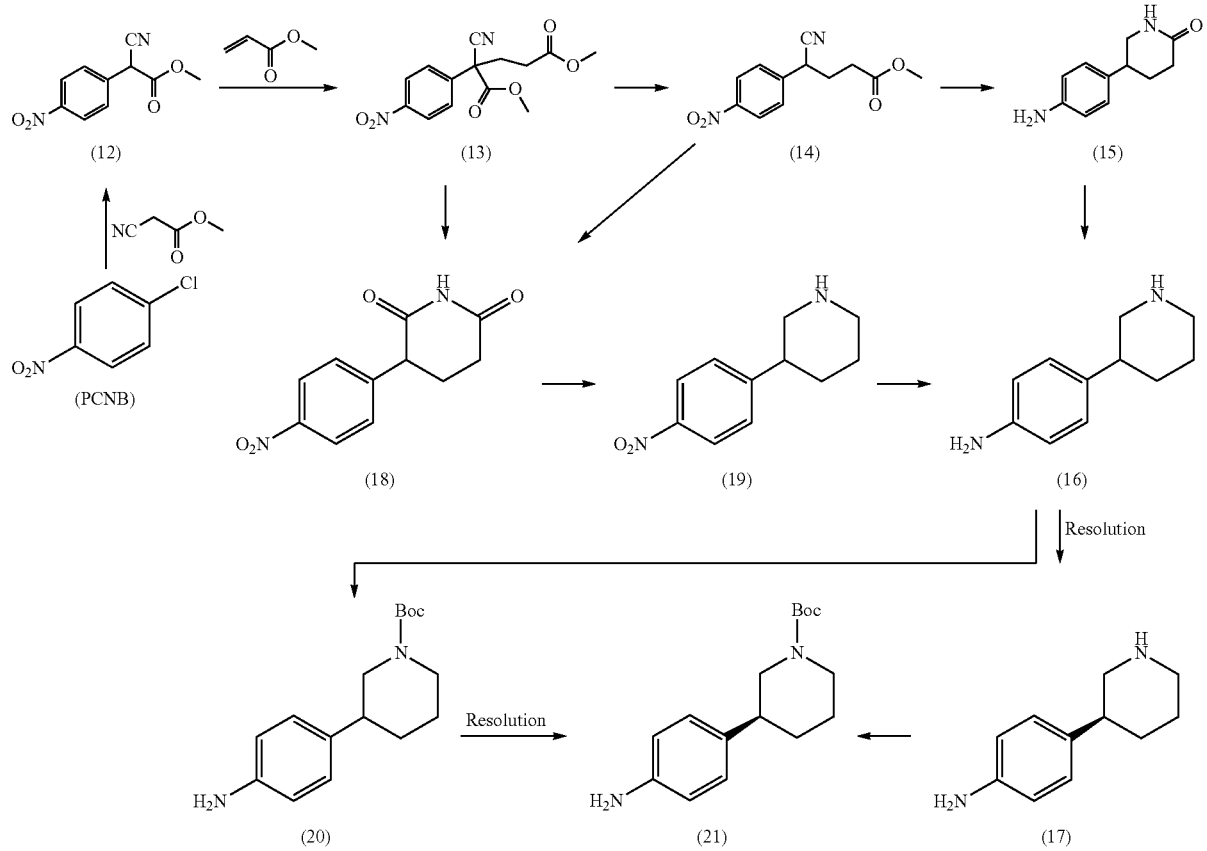

In a further embodiment, compound of formula (12) is prepared by reacting 4-chloro nitro benzene (PCNB) with methyl cyanoacetate in the presence of base in a suitable solvent.

Suitable solvents that may be used include, but are not limited to polar aprotic solvents, Preferably, the solvent may be selected from the group comprising of DMSO, DMA, DMF or the like, and any mixtures thereof.

Suitable base that may be used includes, but is not limited to inorganic base. Preferably, the base may be Potassium bicarbonate, Potassium carbonate, Sodium Carbonate.

Compound of formula (13) is prepared by reacting compound of formula (12) with methyl acrylate in the presence of base in a suitable solvent.

Suitable solvents that may be used include, but are not limited to ether solvents. Preferably, the solvent may be selected from the group comprising of THF, 2-Me THF or the like, and any mixtures thereof.

Suitable base that may be used includes, but is not limited to organic base. Preferably, the base may be N-methylmorpholine Compound (14) is obtained by decarboxylation of compound (13) in the presence of a base.

Suitable base that may be used includes, but is not limited to inorganic base. Preferably, the base may be Sodium bicarbonate, Sodium carbonate.

In another embodiment, the present disclosure provides process for the preparation of compound of formula (15) by hydrogenation of compound of formula (14) with suitable hydrogenating agent in a suitable solvent at suitable pressure and temperature.

The suitable hydrogenating agent may include, but is not limited to, $H_2$/Ni.

Suitable solvents that may be used include, but are not limited to: alcohol solvents, ether solvents, or the like. Preferably, the solvent may be selected from the group comprising methanol, ethanol, IPA, THF, 2-Me THF, and mixtures thereof.

The process may be carried out at a temperature from about 30° C. to about 100° C., preferably at about 50° C. to about 60° C.

The process may be carried out at about 2 $Kg/cm^2$ to about 10 $Kg/cm^2$ pressure of hydrogen gas. Preferably the process may be carried out at about 6 $Kg/cm^2$ to about 8 $Kg/cm^2$ pressure of hydrogen gas.

In another embodiment, the present disclosure provides process for the preparation of compound of formula (16) by reducing compound of formula (15) in presence of a suitable reducing agent in a suitable solvent at suitable temperature.

The suitable reducing agent may include, but are not limited to, borane dimethyl sulfide complex ($BH_3$-DMS), borane tetrahydrofuran complex ($BH_3$-THF), lithium borohydride ($LiBH_4$), $NaBH_4/BF_3$ etherate or the like, or any mixtures thereof.

Suitable solvents that may be used include, but are not limited to: ether solvents, or the like. Preferably, the solvent may be selected from the group comprising THF, 2-Me-THF, monoglyme, diglyme and mixtures thereof.

The process may be carried out at a temperature from about −20° C. to about 100° C., preferably at about −10° C. to about 30° C.

Optionally, compound of formula (16) may be isolated as an acid addition salt. Preferably, compound of formula (16) may be isolated as benzoate, maleate, succinate, or sulphate salt of compound of formula (16).

Typically, the isolation of the compound of formula (16) as an; acid addition salt, increase its purity.

Compound (21) is obtained by N-protection of compound (16) or its acid addition salt; followed by chiral resolution; or alternatively by chiral resolution of compound (16) followed by N-protection of compound 17; according to methods known in the literature e.g., U.S. Pat. No. 8,071, 623.

Niraparib tosylate monohydrate can be prepared according to any of the processes known in the literature, for example WO 2008/084261; or according to the processes as described herein under examples for Niraparib tosylate monohydrate.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

X-Ray Powder Diffraction Method:
X-Ray Diffraction Was Performed on X-Ray Powder Diffractometer:
Bruker D8 Advance; CuK_radiation (λ=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.
Measurement Parameters:
Scan range: 2-40 degrees 2-theta;
Scan mode: continuous;
Step size: 0.05 degrees;
Time per step: 0.5 s;
Sample spin: 30 rpm;
Sample holder: PMMA specimen holder ring.
NMR: NMR Spectra were taken on a Bruker Avance 400 MHz (400 MHz of frequency for $^1$H NMR and 100.61 MHz of frequency $^{13}$C NMR) at 299K.
Mass Spectra: The ES-MS spectra were taken on ABSCIEX 4600 Q TOF instrument.

EXAMPLES

Example 1: Preparation of
3-formyl-2-nitrobenzamide (Compound 11)

Example 1 (A): Preparation of methyl
3-formyl-2-nitrobenzoate (Compound 10)

To a solution of methyl 3-methyl-2-nitrobenzoate (250 g) in DMF (500 mL) at 25-35° C., dimethylformamide dimethylacetal (DMF-DMA) (621 mL, 4.64 mole) was added. The resulting solution was heated to 130° C.; and stirred until HPLC/TLC analysis indicated completion of reaction. After completion of the reaction, the reaction mass was cooled to 20-30° C.; and water (3.0 L) and sodium periodate (493 g) was charged under stirring. The reaction was allowed to heat at 35-45° C. under stirring until HPLC/TLC analysis indicated completion of reaction. After completion of the reaction, the reaction mass was cooled to 20-30° C., filtered and washed water (500 mL). The wet cake obtained was charged in ethyl acetate (2.0 L), heated to reflux temperature for 1 h, cooled to 60-65° C. and filtered the inorganic salt (NaIO$_3$). Filtrate was concentrated till 2-3 volume (approximately 0.5 L) remains in reactor. The Reaction mass was cooled down to 0-10° C. by maintaining for 1-3 h. The solid was filtered and washed with chilled ethyl acetate (1 L). The solid material obtained was dried under reduced pressure to afford the titled compound (Yield: 155 g; HPLC Purity: >99.0%).

Example 1 (B): Preparation of methyl
3-formyl-2-nitrobenzoate (Compound 10)

To a solution of methyl 3-methyl-2-nitrobenzoate (5 g) in DMF (23.9 mL) at 25-35° C., dimethylformamide dimethylacetal (DMF-DMA) (12.36 mL) and pyrrolidine (7.58 mL) was added. The resulting solution was heated to 100° C.; and stirred until HPLC/TLC analysis indicated completion of reaction. DMF-DMA was distilled off, and followed by addition of DMF (38 mL) to reaction mass. Reaction mass was added drop wise at 40-45° C. to a separate reactor having solution of sodium periodate (19.67 g) and water (57 mL) maintained at 40-45° C. After complete addition, reaction mass was further stirred for 1.5 h. Reaction mass was cooled to 5-10° C., after completion of reaction. Water (100 mL) was added to reaction mass by maintaining temperature at 5-10° C., and was stirred for 1 h. The solid obtained was filtered, washed with water (100 mL). The wet cake obtained was dissolved in ethyl acetate (37 mL). To the resulting solution, charcoal (0.7 g) was added; and the reaction mixture was stirred for 2 h at 75° C. The reaction mass was cooled to 55° C., filtered and concentrated to a volume (3 mL). The resulting slurry was cooled to 5° C. and stirred for 2 h. The solid was filtered, washed with ethyl acetate (2 mL) and suck dried to afford the titled compound (Yield: 2.0 g; HPLC Purity: 99.89).

Example 1 (C): Preparation of
3-formyl-2-nitrobenzamide (Compound 11)

To a solution of Methyl 3-formyl-2-nitrobenzoate (Compound 10) (25 g) in methanol (250 mL), methanesulfonic acid (4 g) was added at room temperature. The resulting mixture was heated to 50-60° C. until reaction does comply by HPLC/TLC. The reaction solution containing methyl 3-(dimethoxy methyl)-2-nitrobenzoate (Compound 2) was charged in pressure vessel at 20-30°. The ammonia gas pressure (4 kg/cm$^2$) was applied slowly at 20-30° C.; temperature of the mass was raised to 45° C. Ammonia pressure was maintained at 2 kg/cm$^2$ and the mass was heated to 65-70° C.; the pressure was raised to 7-8 kg/cm$^2$. The stirring was continued until HPLC/TLC analysis indicated completion of reaction. After completion of the reaction, the reaction mixture was cooled to room temperature. Solvent was removed under vacuum at 40-45° C.; and stripping was done with 2 volume of toluene (50 mL) to remove methanol. The obtained mass was identified as 3-(dimethoxy methyl)-2-nitrobenzamide (Compound 4). To the obtained reaction mass, water (75 mL) and conc. HCl (50 mL) was added followed by stirring at 30-35° C. until HPLC/TLC analysis indicated completion of reaction. After completion of the reaction, reaction mass was cooled to 20-30° C., and stirred for 1-2 h. The product was filtered and dried under reduced pressure to afford the titled compound (Yield: 19.76 g; HPLC Purity: 98.09).

Example 1 (D): Preparation of methyl 3-(dimethoxy methyl)-2-nitrobenzoate (Compound 2)

To a solution of methyl 3-formyl-2-nitrobenzoate (Compound 10) (25 g) in DCM (250 mL), methanol (15 mL) and catalytic amount of methane sulfonic acid (1-2 drops) was added at room temperature. The resulting reaction mixture contained with 3 Å molecular sieve (MS) (10 g) was refluxed at 35-45° C. for 18-20 h or until HPLC/TLC monitoring indicated completion of reaction. After cooling the reaction mixture to room temperature, triethyl amine was added to make the pH neutral). The solvents were evaporated under vacuum to afford the titled compound as yellowish solid (Yield: 29 g; HPLC Purity: 98.03%).
$^1$H NMR (400 MHz, CDCl$_3$): δ 1.75 (s, 6H), 2.31 (s, 3H), 4.00 (s, 1H), 6.14-6.10 (d, 1H), 6.43-6.37 (m, 2H).
$^{13}$C NMR (100 MHz): δ 50.55, 51.15, 97.25, 122.45, 128.57, 129.32, 129.45, 130.29, 147.07, 162.47.
ES-MS: 224.0 [M+1−MeOH]$^+$ Example 1 (E): Preparation of 3-(dimethoxy methyl)-2-nitrobenzoic Acid (Compound 3)

To a solution of methyl 3-(dimethoxy methyl)-2-nitrobenzoate (Compound 2) (21 g) in THF (210 ml), aq. NaOH solution (133.16 g, 0.3291 mole in 63 mL of water) was added. The biphasic mixture was agitated and heated to 50-55° C. for 4-5 h or until HPLC/TLC analysis indicated completion of reaction. After the mixture was checked for complete ester hydrolysis, it was acidified up to pH 2-3 using 10% aq. HCl solution. Resulting mixture was extracted three times with ethyl acetate (150 mL), and phases were separated. Organic phase was washed with saturated aq. NaCl solution (150 mL) and evaporated under vacuum to afford the titled compound as light yellow solid (Yield: 18.37 g; HPLC Purity: 98%).
$^1$H NMR (400 MHz, CD$_3$OD): δ 3.37 (s, 3H), 5.56 (s, 1H), 7.29 (s, 1H), 7.66-7.62 (t, 1H), 8.01-7.99 (d, 2H), 8.11-8.09 (d, 2H), 9.13 (s, 1H).
$^{13}$C NMR (100 MHz, CD$_3$OD): δ 53.84, 98.80, 122.55, 130.15, 131.30, 131.98, 133.19, 149.05, 168.30.
ES-MS: 240.45 [M−1]$^+$, 210.05 [M+1−MeOH]$^+$ Example 1 (F): Preparation of 3-(dimethoxy methyl)-2-nitrobenzoic Acid (Compound 3)

To a solution of methyl 3-formyl-2-nitrobenzoate (Compound 10) (30 g) in methanol (300 mL), catalytic amount of methane sulfonic acid (0.5 mL) was added at room temperature. The resulting mixture was refluxed at 60-64° C. for 3 h or until HPLC/TLC analysis indicated complete of reaction. After cooling to room temperature, aq. NaOH solution (17.2 g in 45 mL of water) was added. The mixture was agitated and heated to 50-55° C. for 4-5 h or until HPLC/TLC analysis indicated completion of reaction. After completion of the hydrolysis reaction, the solvent was distilled off. Water (300 mL) was added to the reaction mass followed by cooling to 5-10° C. Reaction mass was acidified with 10% aq. HCl solution to attain pH in the range of 2 to 3. The precipitated solid was filtered and washed with water (100 mL) to afford the titled compound (Yield: 31.5 g; HPLC Purity: 98.2%).

Example 1 (G): Preparation of 3-(dimethoxy methyl)-2-nitrobenzamide (Compound 4)

To 3-(dimethoxy methyl)-2-nitrobenzoic acid (Compound 2) (1.6 g), dichloromethane (30 mL) was added under N$_2$ atmosphere; followed by addition of solution of pyridine (0.8 mL) and di-tert-butyl dicarbonate (2.3 mL) in dichloromethane (10 mL). The resulting mixture was aged at 20-25° C. for 1 h. Ammonium bicarbonate (0.63 g) was then added in one portion, and resulting mixture was aged at 20-25° C. for 15-20 h or until HPLC/TLC analysis indicated completion of the reaction. After completion of the reaction, 1 M HCl (up to pH-2) was added slowly, and the layers were separated. The organic phase was washed with saturated aq. NaCl solution (25 mL) and distilled under vacuum to afford the titled compound as off white-light yellow solid (Yield: 1.0 g; HPLC Purity: 92%).
$^1$H NMR (400 MHz, CD$_3$OD): δ 3.34 (s, 6H), 5.67 (s, 1H), 7.67-7.63 (t, 1H), 7.72-7.70 (d, 1H), 7.87-7.85 (d, 1H).
$^{13}$C NMR (100 MHz, CD$_3$OD): δ 52.83, 128.53, 129.68, 130.22, 130.25, 131.26, 147.77, 168.73
ES-MS: 240.03 [M]$^+$ Example 1 (H): Preparation of 3-formyl-2-nitrobenzamide (Compound 11)

To a mixture of 3-(dimethoxymethyl)-2-nitrobenzamide (Compound 4) (5.5 g) and THF (55 mL), 11.65 M HCl (11 mL) and water (11 mL) was added. The reaction mixture was stirred at 60-65° C. for 3 h until consumption of acetal was confirmed by HPLC/TLC monitoring. THF was distilled off to 1-2 V and water was added. The reaction mass was neutralized by 2N sodium hydroxide solution, followed by two times extraction with ethyl acetate (2×50 mL). The combined ethyl acetate filtrate was concentrated on a rotary evaporator to 1-2 volume, followed by cooling at 5-10° C. for 2 h. Solid obtained was filtered and washed with pre-cooled ethyl acetate (10 mL). The material was dried under vacuum at 25° C. to afford the titled compound (Yield: 4 g; HPLC Purity: 97.66%).
$^1$H NMR (400 MHz, DMSO-d6): δ 7.93-7.89 (t, 2H), 8.03-8.01 (dd, 1H), 8.17-8.15 (dd, 1H), 8.36 (s, 1H), 10.01 (s, 1H).
$^{13}$C NMR (100 MHz, DMSO-d6): δ 128.08, 130.64, 132.11, 134.16, 134.37, 147.54, 165.81, 189.50
ES-MS: 195.04 [M+1]$^+$ Example 1 (I): Preparation of 3-formyl-2-nitrobenzamide (Compound 11)

To 3-(dimethoxy methyl)-2-nitrobenzoic acid (Compound 2) (10 g), toluene (100 mL) was added under N$_2$ atmosphere, followed by the addition of pyridine (5.02 mL) and di-tertbutyl carbonate (13.58 mL); and the resulting mixture was stirred at 20-25° C. for 1 h. Ammonium bicarbonate (3.93 g) was added to the reaction mixture and was stirred at 20-25° C. for 15-20 h or until HPLC/TLC analysis indicated completion of reaction. After completion of the reaction, brine solution (100 mL) was added and the mass was stirred for 0.5 h. Organic layer was separated and washed with 10% aq. HCl solution (25 mL). To the organic layer conc. HCl (5 mL) in water (10 ml) was added and the mass was heated to 60-65° C. for 3 h. After completion of reaction, solid precipitated was filtered and washed with water (2×25 mL). The material was dried under vacuum at 25° C. to afford the titled compound (Yield: 5.5 g; HPLC Purity: 99.48%).

Example 2: Preparation of tert-butyl (S)-3-(4-aminophenyl) piperidine-1-carboxylate (Compound 21)

Example 2 (A): Preparation of methyl 2-cyano-2-(4-nitrophenyl) Acetate (Compound 12)

To a solution of 4-chloro nitro benzene (PCNB) (100 g) in DMF (500 mL), Charged $K_2CO_3$ (219 g) and methyl cyanoacetate (157.2 g) was charged. The suspension was heated to 110-120° C. until HPLC/TLC analysis indicated completion of reaction. After the completion of reaction, the reaction mass was cooled to 10-20° C. and water (500 mL) was charged. Reaction mass was acidified with dilute $H_2SO_4$ to adjust the pH in the range of 2.0-2.5 to precipitate the solid. Water (1500 mL) was charged to reaction mass, stirred for 1 h, filtered and washed two times with water (200 mL). The solid obtained was dried under vacuum at 55° C. to give crude product. Crude product obtained was charged to reactor followed by addition of 3 V of toluene (500 mL) and maintained for 30-45 minutes at 60-70° C. The reaction mass was cooled to 5-10° C., and maintained at 5-10° C. for 1-2 hrs. The solid obtained was filtered and dried in vacuum oven at 50-55° C. to afford the titled compound (Yield: 107 g; HPLC Purity: >99%).

Example 2 (B): Preparation of dimethyl 2-cyano-2-(4-nitrophenyl) Pentanedioate (Compound 13)

To a solution of methyl 2-cyano-2-(4-nitrophenyl) acetate (Compound 12) (40 g) in THF (1000 mL), NMP (19.29 g) and methyl acrylate (16.42 g) was charged. The reaction mass was heated at 50-55° C. until HPLC/TLC analysis indicated completion of reaction. After completion of the reaction, reaction mixture was diluted with water (120 mL), followed by distillation under vacuum at 45-50° C. to remove THF. Water (200 mL) was charged to reaction mass and the product was extract in ethyl acetate (200 mL). Aqueous layer was again extracted with ethyl acetate (200 mL). Combined organic layer was washed with water (100 mL). Organic layer was distilled under vacuum at 40-55° C. to give crude product. Crude product obtained was charged to reactor followed by addition of 7 V of isopropyl alcohol (500 mL). The reaction mass was heated to 60-70° C. and maintained for 30-45 minutes. The reaction mass was cooled to 0-10° C. and further maintained for 1-2 h. The solid obtained was filtered and dried in vacuum oven at 50-55° C. to afford the titled compound (Yield: 35 g; HPLC Purity: >96%).

Example 2 (C): Preparation of methyl 4-cyano-4-(4-nitrophenyl) Butanoate (Compound 14)

To a solution of dimethyl 2-cyano-2-(4-nitrophenyl)pentanedioate (Compound 13) (29 g) in tetrahydro furan (145 mL), $Na_2CO_3$ (20.07 gm) in water (290 mL) was charged. The reaction mass was heated heated to reflux until HPLC/TLC analysis indicated completion of reaction. After the completion of reaction, reaction mixture was distilled under vacuum at 50° C. to remove THF. Reaction mass was diluted with ethyl acetate (145 mL) and layers were separated. Aqueous layer was again extracted with ethyl acetate (145 mL); and combined organic layer was washed with water (80 mL). Organic layer was distilled under vacuum at 40-55° C. to afford the titled compound as an oily mass (Yield: 20 g; HPLC Purity: 96.96%).

Example 2 (D): In-Situ Preparation of methyl 4-cyano-4-(4-nitrophenyl) Butanoate (Compound 14)

To a solution of methyl 2-cyano-2-(4-nitrophenyl) acetate (Compound 12) (5 g) in tetrahydro furan (50 mL), N-methyl morpholine (2.41 g) and methyl acrylate (2.05 g) was charged. The reaction mass was heated at 50-55° C. until HPLC/TLC analysis indicated completion of reaction. After the completion of reaction, water (25 mL) was charged and distilled under vacuum to remove THF at 45-55° C. $Na_2CO_3$ (6.01 g) in water (50 mL) and THF (15 mL) was charged; and the reaction mass was heated to reflux till the completion of reaction. After the completion of reaction, reaction mixture was distilled under vacuum at 50° C. to remove THF. Reaction mass was diluted with ethyl acetate (30 mL) and layers were separated. Aqueous layer was again extracted with ethyl acetate (20 mL), and combined organic layer was washed with water. Organic layer was distilled under vacuum at 40-55° C. to afford the titled compound (Yield: 5 g; HPLC Purity: >90%).

Example 2 (E): Preparation of 5-(4-aminophenyl)piperidin-2-one (Compound 15)

To a solution of methyl 4-cyano-4-(4-nitrophenyl)butanoate (Compound 14) (5 g) in methanol (35 mL) in a hydrogenator, Raney nickel (2.5 g) was charged and heated to 60-65° C. under 8-10 kg/cm² pressure of hydrogen gas till the completion of reaction. After the completion of reaction, reaction mixture was cooled to 25-30° C., filtered through celite bed and washed with methanol (10 mL). The filtrate was distilled under vacuum at 50° C. to afford the solid. Solid obtained was suspended in MTBE (15 mL), stirred for 0.5 h, filtered, washed with MTBE (10 mL) and dried under vacuum at 50° C. to afford the titled compound (Yield: 2.2 g; HPLC Purity: 93.76%).

Example 2 (F): Preparation of 3-(4-nitrophenyl)piperidine-2,6-dione (Compound 18)

To a solution of dimethyl 2-cyano-2-(4-nitrophenyl)pentanedioate (Compound 13) (5.) in acetic acid (20 mL), concentrated $H_2SO_4$ (8 g) was charged. The reaction mass was heated to 100-110° C. until HPLC/TLC analysis indicated completion of reaction. After completion of reaction, the reaction mixture was cooled to ambient temperature and poured into ice water mixture. The pH was adjusted to neutral using 3M NaOH solution. Reaction mass was diluted with ethyl acetate (25 mL) and layers were separated. Aqueous layer was again extracted with ethyl acetate (25 mL), and combined organic layer was washed with saturated sodium bicarbonate solution (25 mL). Organic layer was distilled under vacuum at 40-55° C. to give crude product, which was further purified by column chromatography over silica gel (60-120 mesh) using 40% ethyl acetate/hexane as eluent to afford the titled compound (Yield: 0.89 g; HPLC Purity: 97.88%).

Example 2 (G): Preparation of 3-(4-nitrophenyl)piperidine-2,6-dione (Compound 18)

To a solution of methyl 4-cyano-4-(4-nitrophenyl)butanoate (Compound 14) (10 g) in toluene (50 mL), concentrated sulphuric acid (9.87 g) and acetic acid (6.04 g) was charged.

The reaction mass was heated to reflux until HPLC/TLC analysis indicated completion of reaction. After completion of reaction, the reaction mixture was cooled to ambient temperature and diluted with water (50 mL). Toluene was distilled under vacuum at 45-50° C. Reaction mass was diluted with ethyl acetate (50 mL) and layers were separated. Aqueous layer was again extracted with ethyl acetate (50 mL), and combined organic layer was washed with brine solution (30 mL). Organic layer was distilled under vacuum at 40-55° C. to afford the solid. The solid obtained was suspended in 50 ml of cyclohexane, stirred for 15-30 minutes, filtered and dried under vacuum at 50° C. to afford titled compound (Yield: 3.0 g; HPLC Purity: 88.9%).

Example 2 (H): Preparation of 3-(4-nitrophenyl)piperidine (Compound 19)

To the suspension of 3-(4-nitrophenyl)piperidine-2,6-dione (Compound 18) (2.3 g) in THF (25 mL), NaBH$_4$ (1.11 g) and BF$_3$.etherate (4.18 g) was charged at 0-10° C. The reaction mixture was maintained at 0-10° C. for 1 h followed by rising the temperature to ambient temperature until HPLC/TLC analysis indicated completion of reaction. After completion of reaction, reaction mass was cooled to 0-5° C., and 50% acetic acid solution in water (6 mL) was slowly added and further allowed to warm to ambient temperature. THF was distilled off under vacuum at 45-50° C., and reaction mass was diluted with water (25 mL) and MTBE (25 mL). Layers were separated and aqueous layer was again extracted with MTBE (25 mL). Combined MTBE layers were discarded and the product was extracted from aqueous layer using n-butanol. n-Butanol layer was distilled off under vacuum at 50-55° C. to afford the titled compound (Yield: 1.2 g; HPLC Purity: 81.17%).

Example 2 (I): Preparation of 4-(piperidin-3-yl)aniline (Compound 16)

To a solution of 3-(4-nitrophenyl)piperidine (Compound 19) (1.0 g) in methanol (20-40 mL) in hydrogenator, 50% wet Pd/C (100-200 mg) was charged. The reaction mixture was heated to 50-60° C. under a hydrogen gas pressure of 6-8 kg/cm$^2$ till the completion of reaction. After completion of reaction, reaction mixture was cooled to 25-30° C., filtered it through celite bed and washed with methanol (5 mL). The filtrate was distilled under vacuum at 50° C. to afford the titled compound (Yield: 0.5 g; HPLC Purity: 76.10%).

Example 2 (J): Preparation of 4-(piperidin-3-yl) Aniline (Compound 16)

To the suspension of 5-(4-aminophenyl) piperidin-2-one (Compound 15) (15 g) in THF (150 mL), NaBH$_4$ (8.95 g) and BF$_3$.etherate (3.357 g) was charged at 0-10° C. The reaction mixture was maintained for 4-6 h or until HPLC/TLC analysis indicated completion of reaction. After completion of reaction, reactions mass was cooled to 0-5° C. and slowly quenched with 5M HCl solution (100 mL). The reaction mass was heated to 60-65° C. and maintained for 1 h. Reaction mass was cooled to 0-10° C. and basified with 5M NaOH solution till pH>13.0. THF was distilled off under vacuum at 45-50° C. and residue was extracted with isopropyl acetate (75 mL). Organic layer was distilled off under vacuum at 50-55° C. to afford the titled compound (Yield: 12.10 g; HPLC Purity: 95.66%).

Example 2 (K): Preparation of Benzoate Salt of 4-(piperidin-3-yl) Aniline (Benzoate Salt of Compound 16)

To a mixture of 4-(piperidin-3-yl) aniline (Compound 16) (0.5 g) in acetone (5 mL), benzoic acid (0.38 g) was charged at reflux temperature. The reaction mass was stirred at reflux temperature for 30 minute. The reaction mass was cooled to 20-25° C. and stirred further for 3.5 h. The solid obtained was filtered, washed with acetone (3 mL) and dried under vacuum at 50-55° C., to afford the titled compound (Yield: 0.64 g; HPLC Purity: >97.50%).

Example 2 (L): Preparation of Maleate Salt of 4-(piperidin-3-yl) Aniline (Maleate Salt of Compound 16)

To a mixture of 4-(piperidin-3-yl) aniline (Compound 16) (0.5 g) in acetone (5 mL), maleic acid (0.36 g) was charged at reflux temperature. The reaction mass was stirred at reflux temperature for 30 minute. The reaction mass was cooled to 20-25° C. and stirred further for 3 h. The solid obtained was filtered, washed with acetone (3 mL) and dried under vacuum at 50-55° C. to afford the titled compound (Yield: 0.6 g; HPLC Purity: >98.80%).

Example 2 (M): Preparation of Succinate Salt of 4-(piperidin-3-yl) Aniline (Succinate Salt of Compound 16)

To a mixture of 4-(piperidin-3-yl) aniline (Compound 16) (0.5 g) in acetone (5 mL), succinic acid (0.36 g) was charged at reflux temperature. The reaction mass was stirred at reflux temperature for 30 minute. The reaction mass was cooled to 20-25° C. and stirred further for 3 h. The solid obtained was filtered, washed with acetone (3 mL) and dried under vacuum at 50-55° C. to afford the titled compound (Yield: 0.63 g; HPLC Purity: >95.0%).

Example 2 (N): Preparation of Sulfate Salt of 4-(piperidin-3-yl) Aniline (Sulfate Salt of Compound 16)

To a mixture of 4-(piperidin-3-yl) aniline (Compound 16) (1.0 g) in methanol (7 mL), sulfuric acid (0.83 g) was charged at 20-30° C. The reaction mass was stirred at 20-30° C. for 6 h. The solid obtained was filtered, washed with acetone (4 mL) and dried under vacuum at 50-55° C. to afford the titled compound (Yield: 1.30 g; HPLC Purity: >98.9%).

Example 2 (O): Preparation of tert-butyl 3-(4-aminophenyl) piperidine-1-carboxylate (Compound 20)

A mixture of 4-(piperidin-3-yl) aniline (Compound 16) (2.0 g) in methanol (10 mL) and water (5 mL) in a reactor was cooled to 0-5° C. NaOH (1.81 g) and Boc anhydride (2.59 g) was slowly charged with stirring to the reaction mixture. The reaction mass was stirred at 5-10° C. and then allowed to warm up to 20° C. until HPLC/TLC analysis indicated completion of reaction. The product was filtered, washed with water (6 mL) and methanol (2 mL) mixture. The solid was dried under vacuum at 50-55° C. to afford the titled compound (Yield: 2.67 g; HPLC Purity: >95.0%).

Example 2 (P): Preparation of dibenzoyl-L-tartaric Acid Salt of tert-butyl 3-(4-aminophenyl) piperidine-1-carboxylate (dibenzoyl-L-tartaric Acid Salt of Compound 20)

To a mixture of tert-butyl 3-(4-aminophenyl) piperidine-1-carboxylate (Compound 20) (0.5 g) in ethyl acetate (3.8 mL) and methanol (0.2 mL) in a reactor, dibenzoyl-L-tartaric acid (0.65 g) was added at 20-25° C. and followed by stirring for 5-6 h at 20-25° C. The solid obtained was filtered, washed with MTBE (2 mL) and dried under vacuum at 50-55° C. to afford the titled compound (Yield: 0.18 g; Chiral Purity: >80% of Desired S-isomer).

Example 2 (Q): Preparation of tert-butyl (S)-3-(4-aminophenyl) piperidine-1-carboxylate (Compound 21)

To a mixture of L-tartaric acid salt of tert-butyl (S)-3-(4-aminophenyl) piperidine-1-carboxylate (L-tartaric acid salt of Compound 20) (104 g) in ethyl acetate (500 mL) and water (500 mL) in a reactor, $Na_2CO_3$ (32.31 g) was added slowly at 20-30° C. and stirred for 1-2 h. Layers were settled separated. The organic layer was washed with water (300 mL). The organic layer was concentrated to afford the titled compound (Yield: 0.63 g; Chiral Purity: >99.96% of Desired S-isomer).

Example 2(R): Preparation of tert-butyl 3-(4-aminophenyl) piperidine-1-carboxylate (Compound 20)

Preparation of 5-(4-aminophenyl)piperidin-2-one (Compound 15)

To a solution of 4-chloro nitro benzene (PCNB) (100 g) in DMSO (400 mL), $K_2CO_3$ (219.2 g) and methyl cyanoacetate (141.5 g) were charged. The suspension was heated to 110-120° C. After the completion of reaction, the reaction mass was cooled to 10-20° C.; water (300 mL) and toluene (100 mL) were charged. Reaction mass was acidified with dilute $H_2SO_4$ to adjust the pH in the range of 2.0-2.40 to precipitate the solid, stirred for 2-3 h, filtered and washed with water (200 mL). The obtained solid was stirred with 2-Me THF (500 mL) at 40-45° C. for 1-2 h, filtered and washed with 200 mL of 2-Me THF to remove inorganic salts. To the combined organic layer, N-methyl morpholine (70.6 g) and methyl acrylate (60.1 g) were charged. The reaction mass was heated and stirred at 50-55° C. until HPLC/TLC analysis indicated completion of reaction. The reaction mass was distilled under vacuum till 3.0-4.0 vol of reaction mass remained inside the reactor. Aqueous solution of $Na_2CO_3$ (100 gm in 800 mL of water) was then charged and the reaction mass was stirred at 60-65° C. After the completion of reaction (HPLC/TLC), the mixture was distilled under vacuum at 50° C. to remove 2-Me THF. Reaction mass was diluted with toluene (500 mL) and layers were separated. Aqueous layer was again extracted with toluene (300 mL) and the combined organic layer was washed with water (300 mL). Organic layer was distilled under vacuum at 50-55° C. to afford the oily crude compound. The oily compound was dissolved in methanol (500 mL), Raney nickel (30 g) was charged and the mixture was heated to 60-65° C. under 8-10 kg/cm² pressure of hydrogen gas till the completion of reaction. The reaction mixture was cooled to 25-30° C., filtered through celite bed and washed with methanol (200 mL). The filtrate was distilled under vacuum at 50° C. to afford the solid. The obtained solid was suspended in ethyl acetate (300 mL), heated (50-60° C.) and stirred for 30-60 minutes. The mixture was slowly cooled to 10-15° C., filtered, and washed with ethyl acetate (50 mL). The solid was dried under vacuum at 50° C. to afford compound 15 (Yield: 60 g; HPLC Purity: 94.94%).

Preparation of Sulfate Salt of 4-(piperidin-3-yl) aniline (Sulfate Salt of Compound 16)

To the suspension of 5-(4-aminophenyl) piperidin-2-one (Compound 15) (165 g) in THF (1650 mL), $NaBH_4$ (73.8 g) and $BF_3$.etherate (369.2 g) were charged at 0-10° C. The reaction mixture was maintained at this temperature until reaction was completed (HPLC/TLC). The reaction mass was cooled to 0-5° C. and slowly quenched with HCl (5M solution; 660 mL). Reaction mass was stirred at 25-35° C. (2-3 h), heated to 60-65° C. and maintained for 1 h. Reaction mass was distilled under vacuum at 50° to remove THF. The mixture was cooled to 0-10° C. and basified with NaOH (5M solution; pH 11.75-12.5). Reaction mass was diluted with isopropyl acetate (990 mL) and layers were separated. The aqueous layer was again extracted with isopropyl acetate (660 mL) and the combined organic layer was distilled off under vacuum at 50-55° C. to afford compound 16 as free base. Methanol (1155 mL) and $H_2SO_4$ (85 gm) were added at 25-40° C. and the mixture was stirred (2-4 h). Solid precipitated out, filtered and washed with methanol (165 mL). The product was dried under vacuum at 50° C. to afford the sulfate salt of compound 16 (Yield: 160 g; HPLC Purity: 94.79%).

Preparation of tert-butyl 3-(4-aminophenyl) piperidine-1-carboxylate (Compound 20)

To a solution of the sulfate salt of 4-(piperidin-3-yl) aniline (sulfate salt of compound 16) (150 g) in methanol (2110 mL) and water (1050 mL), NaOH (109.30 g) and Boc anhydride (188.44 g) were slowly charged with stirring. The reaction mass was stirred at 40-45° C. until HPLC/TLC analysis indicated completion of reaction. Water (3000 mL) was charged and stirred for 2 h. The solid product was filtered, washed with water (600 mL) and dried under vacuum at 50-55° C. to afford compound 20 (Yield: 151 g; HPLC Purity: 98.40%).

Example 3: Preparation of (S)-2-(4-(piperidin-3-yl) phenyl)-2H-indazole-7-carboxamide Tosylate Monohydrate (Niraparib Tosylate Monohydrate)

Example 3 (A): Preparation of tert-butyl (E)-3-(4-((3-carbamoyl-2-nitrobenzylidene)amino)phenyl) piperidine-1-carboxylate (Compound 5) (Compound II, $R_5$ is H and $R_6$ is Boc)

3-Formyl-2-nitrobenzamide (Compound 11) (35.0 g), tert-butyl (S)-3-(4-aminophenyl)piperidine-1-carboxylate (Compound 21) (52.31 g) and methanol (210 mL) were charged to a vessel under inert atmosphere and heated to 65° C. for 4 h or until HPLC/TLC analysis indicated completion of reaction. After completion of the reaction, the slurry was cooled to 20-25° C., filtered, washed with methanol (35 mL) and dried under reduced pressure to afford the titled compound (Yield: 73.8 g; HPLC Purity: 99.85%).

¹H NMR (400 MHz, DMSO-d6): δ 1.41 (s, 9H), 1.64 (m, 2H), 1.91-1.88 (d, 1H), 2.64 (s, 1H), 2.77 (s, 1H), 3.96 (d, 2H), 7.25 (s, 2H), 7.34 (s, 2H), 7.86-7.82 (m, 3H), 8.23 (s, 1H), 8.35 (s, 1H), 8.55 (s, 1H).

$^{13}$C NMR (100 MHz, DMSO-d6): δ 21.87, 25.51, 28.56, 31.79, 42.17, 79.14, 121.81, 128.47, 131.13, 131.42, 131.67, 143.17, 148.79, 149.11, 154.35, 154.50, 166.42.

ES-MS: 353.17 [M+1−Boc]$^+$

Example 3 (B): Preparation of tert-butyl (E)-3-(4-((3-carbamoyl-2-nitrobenzylidene)amino)phenyl) piperidine-1-carboxylate (Compound 5) (Compound II, $R_5$ is H and $R_6$ is Boc)

To a solution of methyl 3-methyl-2-nitrobenzoate (compound 8) (300 g) in DMF (1500 mL) at 25-35° C., dimethylformamide dimethylacetal (DMF-DMA) (668.72 g, 5.61 mole) was added. The resulting solution was heated to 122-130° C.; and stirred until HPLC/TLC analysis indicated completion of reaction. After completion of the reaction, the reaction mass was cooled to 20-30° C.; and water (3.6 L) and sodium periodate (591.75 g) were charged under stirring. The reaction was allowed to heat at 35-55° C. under stirring until HPLC/TLC analysis indicated completion of reaction. After completion of the reaction, the reaction mass was cooled to 20-30° C., filtered and washed with water (600 mL). The obtained wet cake was charged in ethyl acetate (2.4 L), heated to reflux temperature for 1 h, cooled to 60-65° C. and filtered the inorganic salt (NaIO3). Filtrate was concentrated (to volume of 600 mL-900 mL); Methanol (900 mL) was added to the mass and the solvent was removed under vacuum leaving 600 mL-900 mL in the reactor. Methanol (2250 mL) and Methanesulphonic acid (4.98 mL) were added at room temperature and the reaction was stirred at 55-65° C. (monitored by HPLC/TLC). The reaction solution containing methyl 3-(dimethoxy methyl)-2-nitrobenzoate (Compound 2) was charged in pressure vessel at 20-30°. The ammonia gas pressure (4 kg/cm$^2$) was applied slowly at 20-30° C.; temperature of the mass was raised to 45° C. Ammonia pressure was maintained at 2 kg/cm$^2$ and the mass was heated to 65-70° C.; the pressure was raised to 7-8 kg/cm$^2$. The stirring was continued until HPLC/TLC analysis indicated completion of reaction. After completion of the reaction, the mixture was cooled to room temperature. Solvent was removed under vacuum at 40-45° C.; and stripping was done with 3 volume of toluene (900 mL) to remove methanol. The obtained mass was identified as 3-(dimethoxy methyl)-2-nitrobenzamide (Compound 4). To the obtained reaction mass, water (1500 mL) and conc. HCl (300 mL) were added followed by stirring at 40-50° C. After completion of the reaction, reaction mass was cooled to 25-35° C. and stirred for 1-2 h. The product was filtered, washed with water (2×600 mL), IPA (3×300 mL) and suck dried filtered under reduced pressure to afford wet 3-Formyl-2-nitrobenzamide (Compound 11) (Yield: 276 g (wet), 186.47 g (dry); HPLC Purity: 96.90).

3-Formyl-2-nitrobenzamide (Compound 11) (252 g), tert-butyl (S)-3-(4-aminophenyl) piperidine-1-carboxylate (Compound 21, can be prepared according to example 2(Q)) (230 g) and IPA (1020 mL) were charged to a vessel under inert atmosphere and heated to 74-82° C. for 4-6 h or until HPLC/TLC analysis indicated completion of reaction. After completion of the reaction, the slurry was cooled to 20-30° C., filtered, washed with IPA (2×170 mL) and dried under reduced pressure at 55-65° C. to afford the title compound (Yield: 341 g; HPLC Purity: 98.21%).

Example 3 (C): Preparation of tert-butyl (S)-3-(4-(7-carbamoyl-2H-indazol-2-yl) phenyl)piperidine-1-carboxylate (Compound Va) (Compound V, $R_5$ is H and $R_6$ is Boc=Compound 22)

tert-butyl-(E)-3-(4-((3-carbamoyl-2-nitrobenzylidene) amino)phenyl)piperidine-1-carboxylate (Compound II, $R_5$ is H and $R_6$ is Boc) (Compound 5) (25 g), sodium azide (5.4 g), 2,6-lutidine (5.89 g) and DMF (175 mL) were charged to a round bottomed flask under nitrogen atmosphere. The reaction mixture was heated to 120° C. for 8 h or until HPLC/TLC analysis indicated completion of the reaction. After cooling the reaction mass to 70° C., toluene (125 mL) and water (125 mL) were added. The reaction mass was further cooled 60° C., stirred for 0.5 h and the layers were separated. The organic layer was washed with 3% aq. NaHCO$_3$ solution (125 mL). The solvent was removed under vacuum at 50° C. and stripping was done with MTBE (50 mL). MTBE (150 mL) was added, and the mass was refluxed for 0.5 h, slowly cooled to 20-25° C., stirred for 1 h and filtered. The solid was washed twice with MTBE (25 mL) and dried under vacuum at 40° C. to afford the titled compound as a yellow colored solid (Yield: 15.4 g; HPLC Purity: 99.09).

Example 3 (C): Preparation of tert-butyl (S)-3-(4-(7-carbamoyl-2H-indazol-2-yl) phenyl)piperidine-1-carboxylate (Compound Va) (Compound V wherein $R_5$ is H and $R_6$ is Boc=Compound 22)

tert-butyl(E)-3-(4-((3-carbamoyl-2-nitrobenzylidene) amino)phenyl)piperidine-1-carboxylate (Compound II, $R_5$ is H and $R_6$ is Boc) (4 g), sodium azide (0.574 g) and DMF (25 mL) were charged to a vessel under inert atmosphere, followed by the addition of 2,6-lutidine (0.947 g) and the reaction mixture was heated to 110° C. for 20 h or until HPLC/TLC analysis indicated completion of the reaction. After completion of the reaction, the reaction mass was cooled to 25° C., toluene (100 mL) was added followed by addition of 25% aq. LiCl solution (precooled to 5° C.). The layers were separated and aqueous layer was re-extracted twice with toluene (25 mL). The organic layers were combined and washed twice with 25% aq. LiCl solution (30 mL). The organic layer was passed through small silica bed using MTBE:DCM (1:1) (500 mL). Solvent was removed under vacuum until 1-2 volume was left. The mass was cooled to 0-10° C., stirred for 2 h, filtered and suck dried to afford the titled compound (Yield: 1.5 g; HPLC Purity: 92%).

$^1$H NMR (400 MHz, CDCl$_3$): δ 1.51 (s, 9H), 1.72-171 (m, 2H), 1.81-1.80 (d, 2H), 2.81 (s, 1H), 3.23 (s, 1H), 6.18 (s, 1H), 7.30-7.26 (m, 1H), 7.34 (t, 1H), 7.45-7.43 (d, 2H), 7.87-7.85 (d, 1H), 7.93-7.91 (d, 1H), 8.33-8.31 (d, 1H), 8.53 (s, 1H), 9.08 (s, 1H).

$^{13}$C NMR (100 MHz, CDCl$_3$): δ 25.40, 26.99, 28.50, 31.74, 49.48, 72.81, 79.70, 121.07, 121.22, 121.67, 122.48, 123.64, 125.05, 128.41, 130.86, 138.43, 144.89, 154.83, 167.17.

ES-MS: 421.25 [M+1]$^+$

Example 3 (D): Preparation of tert-butyl (S)-3-(4-(7-carbamoyl-2H-indazol-2-yl) phenyl)piperidine-1-carboxylate (Compound Va) (Compound V, $R_5$ is H and $R_6$ is Boc=Compound 22)

3-Formyl-2-nitrobenzamide (Compound 11) (3.5 g), tert-butyl (S)-3-(4-aminophenyl) piperidine-1-carboxylate (Compound 21) (4.98 g) and ethanol (30 mL) were charged to a round bottomed flask under inert atmosphere and heated to reflux temperature for 2 h or until HPLC/TLC analysis indicated completion of the reaction. DMF (50 mL) and lutidine (2.5 mL) was added to reaction mass to give a clear solution. Ethanol was distilled off and sodium azide (1.72 g) was added. The reaction mass was heated to 110° C. for 20 h or until HPLC/TLC analysis indicated completion of the reaction. The reaction mass was cooled to 25° C., THF (200 mL) was added followed by addition of 25% aq. LiCl solution (100 mL, precooled at 5° C.) and the layers were separated. The aqueous layer was re-extracted twice with THF (2×50 mL). The organic layers were combined and washed twice with 25% aq. LiCl solution (30 mL). It was passed through small silica bed using MTBE:DCM (1:1) (500 mL). Solvent was removed under vacuum till 1-2 volume was left. Reaction mass was cooled to 0-10° C. for 2 h. The solid obtained was filtered and suck dried to afford the titled compound as off-white solid (Yield: 2.8 g; HPLC Purity: 98%).

Example 3 (E): Preparation of tert-butyl (S)-3-(4-(7-carbamoyl-2H-indazol-2-yl) phenyl)piperidine-1-carboxylate (Compound Va) (Compound V, $R_5$ is H and $R_6$ is Boc=Compound 22)

tert-butyl(E)-3-(4-((3-carbamoyl-2-nitrobenzylidene) amino)phenyl)piperidine-1-carboxylate (Compound II, R5 is H and R6 is Boc) (Compound 5) (10 g), sodium azide (2.15 g), catalytic cuprous iodide (0.25 g) and DMF (70 mL) were charged to a vessel under inert atmosphere, followed by the addition of diisopropyl ethyl amine (4.28 g); and the reaction mixture was heated to 120° C. for 5 h or until HPLC/TLC analysis indicated completion of the reaction. After completion of the reaction, the reaction mass was cooled to 60° C., toluene (150 mL) was added followed by addition of water (120 mL). The layers were separated and the organic layer was washed with saturated sodium bicarbonate solution (50 mL) at 60° C. The organic layer was concentrated under vacuum at 50° C. to afford crude compound. The crude compound obtained was dissolved in toluene:MTBE (5 mL:60 mL) at 60° C., stirred for 1 h at same temperature and slowly cooled to 25° C. The mass was stirred for 1 h, filtered, washed with MTBE (20 mL) and dried under vacuum at 60° C. to afford the titled compound (Yield: 6.8 g; HPLC Purity: 97.66%).

Example 3 (F): Preparation of tert-butyl (S)-3-(4-(7-carbamoyl-2H-indazol-2-yl) phenyl)piperidine-1-carboxylate (Compound Va) (Compound V, $R_5$ is H and $R_6$ is Boc=Compound 22)

tert-butyl(E)-3-(4-((3-carbamoyl-2-nitrobenzylidene) amino)phenyl)piperidine-1-carboxylate (Compound II, R5 is H and R6 is Boc) (Compound 5) (10 g), sodium azide (2.15 g), catalytic cuprous bromide (0.318 g) and DMF (70 mL) were charged to a vessel under inert atmosphere, followed by the addition of diisopropyl ethyl amine (4.28 g) and the reaction mixture was heated to 120° C. for 5 h or until HPLC/TLC analysis indicated completion of the reaction. After completion of the reaction, the reaction mass was cooled to 60° C., toluene (100 mL) was added followed by addition of water (140 mL). The layers were separated and the organic layer was washed with saturated sodium bicarbonate solution (50 mL) at 60° C. The organic layer was concentrated under vacuum at 50° C. to afford crude compound. The crude compound obtained was dissolved in toluene:MTBE (5 mL:60 mL) at 60° C., stirred for 1 h at same temperature and slowly cooled to 25° C. The mass was stirred for 1 h, filtered, washed with MTBE (20 mL) and dried under vacuum at 60° C. to afford the titled compound (Yield: 6.4 g; HPLC Purity: 98.54%).

Example 3 (G): Preparation of (S)-2-(4-(piperidin-3-yl) phenyl)-2H-indazole-7-carboxamide Tosylate Salt (Niraparib Tosylate Monohydrate)

To a solution of tert-butyl (S)-3-(4-(7-carbamoyl-2H-indazol-2-yl) phenyl)piperidine-1-carboxylate (Compound 22) (15.78 g) in THF (220 mL) and water (11.92 mL), p-toluene sulphonic acid monohydrate (16.14 g) was added under nitrogen atmosphere. The reaction mixture was heated to 65-67° C. and stirred for 16 h or until HPLC/TLC analysis indicated completion of the reaction. After completion of reaction, the slurry was cooled to room temperature, filtered and washed with THF (30 mL). The solid was collected and dried in vacuum at 40° C. to afford the titled compound as tan-colored solid (Yield: 12.5 g; HPLC Purity: 97.34%).

$^1$H NMR (400 MHz, CDCl$_3$): δ 1.85-1.81 (m, 2H), 2.09-2.05 (m, 2H), 2.34 (s, 3H), 3.16-3.04 (m, 3H), 3.49-3.32 (m, 2H), 7.25-7.23 (2H, d,), 7.28-7.26 (2H, d,), 7.51-7.49 (2H, d,), 8.11-7.95 (m, 3H), 8.22-8.15 (dd, 1H), 9.02 (s, 1H).

$^{13}$C NMR (100 MHz, CDCl$_3$): δ 19.91, 22.43, 29.32, 39.49, 43.65, 120.41, 120.78, 121.69, 122.68, 123.85, 125.56, 125.82, 128.22, 128.49, 130.24, 138.90, 140.42, 141.52, 142.07, 146.51, 168.13.

Example 3 (H): Preparation of (S)-2-(4-(piperidin-3-yl) phenyl)-2H-indazole-7-carboxamide Tosylate Salt (Niraparib Tosylate Monohydrate)

To a suspension of tert-butyl (S)-3-(4-(7-carbamoyl-2H-indazol-2-yl) phenyl)piperidine-1-carboxylate (Compound 22) (1 g) in MTBE (4 mL) and water (4 mL) at 0-5° C. was added methanesulphonic acid (3 mL) slowly and the reaction mixture was stirred for 1 h at 0-5° C. The reaction mixture was warmed to 20-25° C. and further stirred for 1 h. MTBE (4 mL) was added to the reaction mass, stirred and layers were separated. To the aqueous layer was added a solution of p-toluene sulphonic acid monohydrate (0.59 g) in water (2 mL) and stirred the mixture for 2 h. The solid was filtered, washed with water (2 mL) and dried under vacuum at 35° C. to afford the titled compound as white solid (Yield: 0.9 g; HPLC Purity: 99.86%).

Example 3 (I): Preparation of (S)-2-(4-(piperidin-3-yl) phenyl)-2H-indazole-7-carboxamide Tosylate Salt (Niraparib Tosylate Monohydrate)

To a suspension of tert-butyl (S)-3-(4-(7-carbamoyl-2H-indazol-2-yl) phenyl)piperidine-1-carboxylate (Compound 22) (1 g) in toluene (4 mL) and water (4 mL) at 0-5° C. was added methanesulphonic acid (3 mL) slowly, and the reaction mixture was stirred for 1 h at the same temperature. The reaction mixture was warmed to 20-25° C. and further stirred for 1 h. The layers were separated. To the aqueous layer a solution of p-toluene sulphonic acid monohydrate (0.59 g) in water (2 mL) was added, stirred the mixture for 2 h, filtered and washed with water (2 mL). The solid obtained was dried under vacuum at 35° C. to afford the titled compound as white solid (Yield: 0.91 g; HPLC Purity: 99.79%).

Example 3 (J): Preparation of (S)-2-(4-(piperidin-3-yl) phenyl)-2H-indazole-7-carboxamide Tosylate Salt (Niraparib Tosylate Monohydrate)

To a suspension of tert-butyl (S)-3-(4-(7-carbamoyl-2H-indazol-2-yl) phenyl)piperidine-1-carboxylate (Compound 22) (1 g) in 2-Me THF (5 mL) and water (2 mL) at 0-5° C., methanesulphonic acid (3 mL) was added slowly and the reaction mixture was stirred for 6 h at 0-5° C. The reaction mixture was warmed to 20-25° C., 2-Me THF (5 mL) and water (5 mL) was further added, stirred the reaction mass and layers were separated. A solution of p-toluene sulphonic acid monohydrate (0.59 g) in water (2 mL) was added to aqueous layer and the mixture was stirred for 1 h. The solid was filtered and washed with water (2 mL). The solid obtained was dissolved in methanol (6 mL) under reflux, cooled the mass to 20-25° C. and stirred for 0.5 h. The reaction mass was further cooled to 0-5° C. and stirred for 1 h. The solid was filtered, washed with chilled methanol (2 mL), and dried under vacuum at 35° C. to afford the titled compound as white solid (Yield: 0.65 g; HPLC Purity: 99.87%).

Example 3 (k): Preparation of (S)-2-(4-(piperidin-3-yl) phenyl)-2H-indazole-7-carboxamide Tosylate Salt (Niraparib Tosylate Monohydrate)

A solution of tert-butyl (S)-3-(4-(7-carbamoyl-2H-indazol-2-yl) phenyl)piperidine-1-carboxylate (Compound 22) (70 g) and p-toluene sulphonic acid monohydrate (95.30 g) in acetone (350 mL) and water (17.5 mL) was stirred and heated to 35-45° C. for 5-8 h. After completion of reaction (monitored by HPLC) the mass was cooled to 20-25° C. and stirred for 1 h. The solid was filtered, washed with acetone (2×70 mL), water (2×70 mL) and acetone (2×70 mL). The product was dried under vacuum at 50-60° C. to afford the title compound as solid (Yield: 71 g; HPLC Purity: 99.92%).

The invention claimed is:

1. A process for preparing Niraparib or a salt thereof; the process comprising the step of reacting compound of formula (III) with compound of formula (IV) to obtain compound of formula (II);

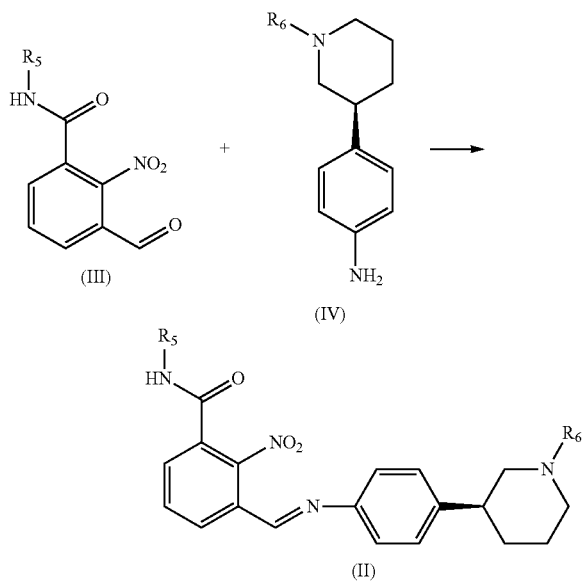

wherein; $R_5$ and $R_6$ can independently be hydrogen, $C_1$-$C_5$ alkyl, and a protecting group; and converting the compound of formula (II) to Niraparib or a salt thereof.

2. A process according to claim 1, wherein the reaction is carried out in a solvent selected from the group consisting of polar aprotic solvents, alcohol solvents, ether solvents, nitrile solvents, hydrocarbon solvents, aromatic hydrocarbon solvents, and mixtures thereof.

3. A process according to claim 2, wherein the solvent is selected from the group comprising of dimethylformamide, N,N-dimethyl acetamide, dimethylsulfoxide, methanol, ethanol, isopropyl alcohol, butanol, acetonitrile, toluene, methyl t-butyl ether, and any mixtures thereof.

4. A process according to claim 1, wherein the reaction is carried out at a temperature from about 0° C. to about 140° C., about 0° C. to about 100° C., or about 40° C. to the reflux temperature.

5. A process according to claim 1, wherein the compound of formula (II) is converted to Niraparib by a process comprising:
(a) cyclizing compound of formula (II) to obtain compound of formula (V);
(b) optionally, deprotecting compound of formula (V) to obtain Niraparib

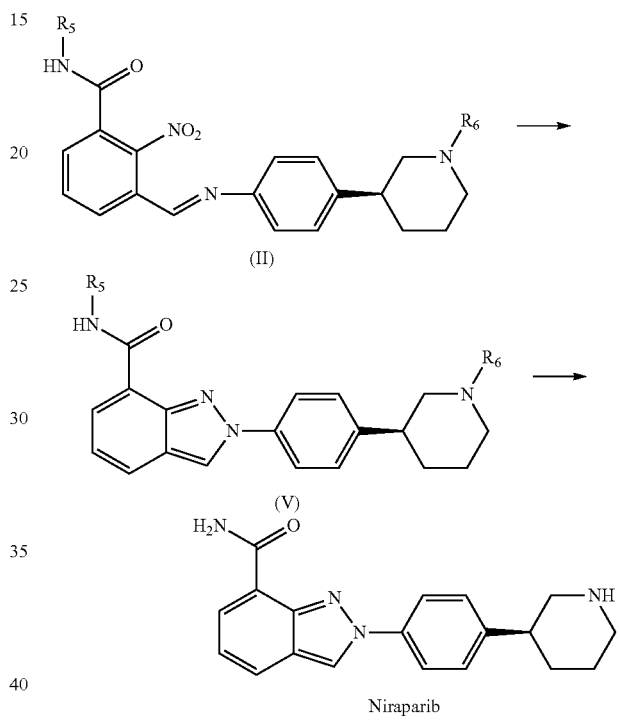

wherein $R_5$ and $R_6$ can independently be hydrogen, $C_1$-$C_5$ alkyl, and a protecting group.

6. A process according to claim 5, wherein step (a) is carried out by employing tetrabutyl ammonium azide, sodium azide or tri-n-butyl phosphine, in a suitable solvent at a suitable temperature; and optionally wherein the reaction is carried out in the presence of a suitable base.

7. A process according to claim 6, wherein the solvent is selected from the group consisting of alcoholic solvents, aromatic hydrocarbon solvent, polar aprotic solvents, and mixtures thereof.

8. A process according to claim 6, wherein the reaction is carried out at a temperature from about 100° C. to about 150° C.

9. A process according to claim 6 wherein the base is, 2,6-lutidine, trimethylamine, N,N-diisopropylethylamine, sodium hydroxide, potassium hydroxide, potassium carbonate or mixtures thereof.

10. A process according to claim 6, wherein the reaction is carried out without a base.

11. A process according to claim 6, wherein step (a) is carried out in the presence of a metal catalyst.

12. A process according to claim 5, wherein the compound of formula (II) is isolated prior to its conversion to the compound of formula (VI).

13. A process according to claim 5, wherein the preparation of the compound of formula (V) is carried out as a one pot reaction without isolating the compound of formula (II).

14. A process according to claim 1, further comprising the step of converting Niraparib into a salt thereof.

15. A process according to claim 1, wherein $R_5$ is hydrogen and $R_6$ is a protective group.

16. A compound selected from

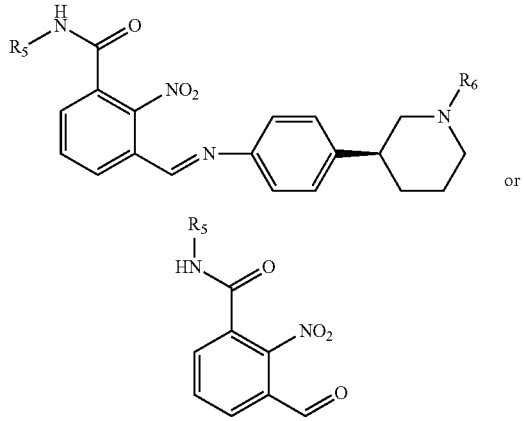

(II)

or (III)

wherein $R_5$ and $R_6$ can independently be hydrogen, $C_1$-$C_5$ alkyl, or a protecting group,

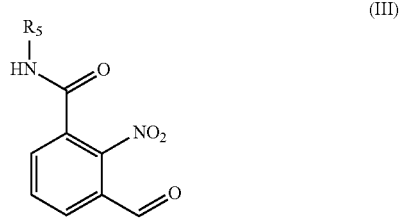

(III)

wherein $R_5$ can be $C_2$-$C_5$ alkyl, or a protecting group.

17. A compound according to claim 16, which is:

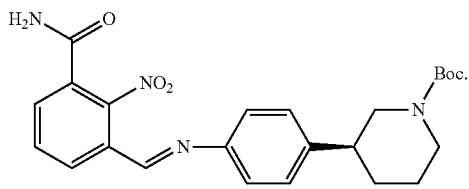

(5)

* * * * *